US010696938B2

United States Patent
Wiles et al.

(10) Patent No.: US 10,696,938 B2
(45) Date of Patent: Jun. 30, 2020

(54) METHOD AND SYSTEM FOR AUTOMATED MICROBIAL COLONY COUNTING FROM STREAKED SAMPLE ON PLATED MEDIA

(71) Applicants: BD KIESTRA B.V., Drachten (NL); Timothy M. Wiles, Manchester, MD (US)

(72) Inventors: Timothy M. Wiles, Manchester, MD (US); Raphael R. Marcelpoil, Corenc (FR)

(73) Assignee: BD KIESTRA B. V., Drachten (NL)

( * ) Notice: Subject to any disclaimer, the term of this patent is extended or adjusted under 35 U.S.C. 154(b) by 66 days.

(21) Appl. No.: 15/567,427

(22) PCT Filed: Apr. 22, 2016

(86) PCT No.: PCT/US2016/028919
§ 371 (c)(1),
(2) Date: Oct. 18, 2017

(87) PCT Pub. No.: WO2016/172532
PCT Pub. Date: Oct. 27, 2016

(65) Prior Publication Data
US 2018/0112173 A1   Apr. 26, 2018

Related U.S. Application Data

(60) Provisional application No. 62/318,488, filed on Apr. 5, 2016, provisional application No. 62/151,688, filed on Apr. 23, 2015.

(51) Int. Cl.
*C12M 1/34* (2006.01)
*G06T 7/00* (2017.01)
(Continued)

(52) U.S. Cl.
CPC ............... *C12M 41/36* (2013.01); *C12Q 1/02* (2013.01); *G06K 9/0014* (2013.01);
(Continued)

(58) Field of Classification Search
None
See application file for complete search history.

(56) References Cited

U.S. PATENT DOCUMENTS 4,700,298 A   10/1987   Palcic
4,724,215 A   2/1988    Farber et al.
(Continued)

FOREIGN PATENT DOCUMENTS

EP   2578693 A1   4/2013
EP   1163362 B1   7/2013
(Continued)

OTHER PUBLICATIONS

PCT International Search Report from PCT Application No. PCT/US2016/028919 dated Nov. 8, 2016.
(Continued)

*Primary Examiner* — Nancy Bitar
(74) *Attorney, Agent, or Firm* — Botos Churchill IP Law LLP

(57) ABSTRACT

An imaging system and method for microbial growth detection, counting or identification. One colony may be contrasted in an image that is not optimal for another type of colony. The system and method provides contrast from all available material through space (spatial differences), time (differences appearing over time for a given capture condition) and color space transformation using image input information over time to assess whether microbial growth has occurred for a given sample.

14 Claims, 20 Drawing Sheets

(51) Int. Cl.
*G06K 9/00* (2006.01)
*C12Q 1/02* (2006.01)

(52) U.S. Cl.
CPC ........ *G06K 9/00147* (2013.01); *G06T 7/0016* (2013.01); *G06T 2207/10056* (2013.01); *G06T 2207/30024* (2013.01)

(56) References Cited

U.S. PATENT DOCUMENTS

| | | | |
|---|---|---|---|
| 5,403,722 A | 4/1995 | Floeder et al. | |
| 5,694,478 A * | 12/1997 | Braier | C12Q 1/04 382/133 |
| 5,723,308 A | 3/1998 | Mach et al. | |
| 5,976,892 A | 11/1999 | Bisconte | |
| 6,122,396 A | 9/2000 | King et al. | |
| 6,385,272 B1 | 5/2002 | Takahashi | |
| 6,605,446 B2 | 8/2003 | Eden | |
| 6,718,077 B1 | 4/2004 | Ferreira et al. | |
| 7,106,889 B1 | 9/2006 | Mahers et al. | |
| 7,298,886 B2 | 11/2007 | Plumb et al. | |
| 7,319,031 B2 | 1/2008 | Vent et al. | |
| 7,351,574 B2 | 4/2008 | Vent | |
| 7,496,225 B2 | 2/2009 | Graessle et al. | |
| 7,582,415 B2 * | 9/2009 | Straus | B82Y 20/00 435/4 |
| 7,666,355 B2 | 2/2010 | Alavie | |
| 7,738,689 B2 | 6/2010 | Plumb et al. | |
| 7,865,008 B2 | 1/2011 | Graessle et al. | |
| 7,957,575 B2 | 6/2011 | Plumb et al. | |
| 8,094,916 B2 * | 1/2012 | Graessle | G01N 15/1475 382/133 |
| 8,131,477 B2 | 3/2012 | Li et al. | |
| 8,260,026 B2 | 9/2012 | Plumb et al. | |
| 8,417,013 B2 | 4/2013 | Bolea et al. | |
| 8,570,370 B2 | 10/2013 | McCollum et al. | |
| 8,588,505 B2 | 11/2013 | Bolea | |
| 8,759,080 B2 | 6/2014 | Graessle et al. | |
| 8,831,326 B2 | 9/2014 | Nishida et al. | |
| 8,840,840 B2 | 9/2014 | Bolea | |
| 8,855,397 B2 | 10/2014 | Moy et al. | |
| 8,895,255 B1 | 11/2014 | Goldberg et al. | |
| 8,896,706 B2 | 11/2014 | van den Hengel et al. | |
| 9,012,209 B2 | 4/2015 | Eden et al. | |
| 9,042,967 B2 | 5/2015 | Dacosta et al. | |
| 9,090,462 B2 * | 7/2015 | Straus | G01N 33/56916 |
| 9,292,729 B2 | 3/2016 | Guthrie et al. | |
| 9,359,631 B2 | 6/2016 | Dupoy et al. | |
| 9,378,545 B2 | 6/2016 | Bise et al. | |
| 9,400,242 B2 | 7/2016 | Allano et al. | |
| 9,470,624 B2 | 10/2016 | Guthrie et al. | |
| 9,567,621 B2 | 2/2017 | Robinson et al. | |
| 9,576,181 B2 | 2/2017 | Allano et al. | |
| 9,606,046 B2 | 3/2017 | Decaux et al. | |
| 10,000,788 B2 * | 6/2018 | Straus | B82Y 20/00 |
| 10,521,910 B2 * | 12/2019 | Wiles | G06K 9/00134 |
| 2003/0227612 A1 | 12/2003 | Fein | |
| 2004/0253660 A1 * | 12/2004 | Gibbs | C12Q 1/045 435/34 |
| 2007/0177149 A1 | 8/2007 | Aronkyto | |
| 2010/0248281 A1 * | 9/2010 | Straus | G01N 33/56916 435/19 |
| 2011/0275110 A1 | 11/2011 | Colin et al. | |
| 2014/0219553 A1 | 8/2014 | van den Hengel | |
| 2014/0278136 A1 * | 9/2014 | Shamsheyeva | C12Q 1/18 702/19 |
| 2015/0225684 A1 | 8/2015 | Spicer | |
| 2015/0268163 A1 | 9/2015 | Dupoy et al. | |
| 2015/0299639 A1 | 10/2015 | Kleefstra et al. | |
| 2015/0339513 A1 | 11/2015 | Bolea | |
| 2015/0353983 A1 | 12/2015 | Drazek et al. | |
| 2016/0060676 A1 | 3/2016 | Lei | |
| 2016/0083686 A1 | 3/2016 | Triva | |
| 2016/0093033 A1 | 3/2016 | Allano et al. | |
| 2016/0098840 A1 | 4/2016 | Allano et al. | |
| 2016/0328844 A1 | 11/2016 | Triva | |
| 2017/0029864 A1 * | 2/2017 | Straus | G01N 33/56916 |
| 2018/0285624 A1 * | 10/2018 | Robinson | G06T 7/0016 |
| 2019/0089828 A1 * | 3/2019 | Li | H04M 1/72569 |

FOREIGN PATENT DOCUMENTS

| | | |
|---|---|---|
| EP | 2430461 B1 | 3/2014 |
| EP | 2287284 B1 | 12/2016 |
| JP | 2005502354 A | 1/2005 |
| WO | 9618720 A1 | 6/1996 |
| WO | 03022999 A2 | 3/2003 |
| WO | 2009061183 A1 | 5/2009 |
| WO | 2013166337 A1 | 11/2013 |
| WO | 2014098994 A1 | 6/2014 |
| WO | 2015114121 A1 | 8/2015 |
| WO | 2015162364 A1 | 10/2015 |
| WO | 2015173490 A1 | 11/2015 |
| WO | 2016001555 A1 | 1/2016 |
| WO | 2016011534 A1 | 1/2016 |
| WO | 2016083744 A1 | 6/2016 |
| WO | 2016097092 A1 | 6/2016 |
| WO | 2016172388 A2 | 10/2016 |
| WO | 2017006055 A1 | 1/2017 |

OTHER PUBLICATIONS

Corkidi, G., et al., "Covasiam: an Image Analysis Method that Allows Detection of Confluent Microbial Colonies and Colonies of Various Sizes for Automated Counting," Applied and Environmental Microbiology, American Society for Microbiology, US, vol. 64, No. 4, pp. 1400-1404, Apr. 1, 1998, (Apr. 1, 1998).

He. V., et al., "Mass Spectrometry Biotyper System Identifies Enteric Bacterial Pathogens Directly from Colonies Grown on Selective Stool Culture Media", Journal of Clinical Microbiology, vol. 48, No. 11, pp. 3888-3892, Sep. 15, 2010, (Sep. 15, 2010).

Turner, Paul, et al., "A Prospective Study of Urinary Pneumococcal Antigen Detection in Healthy Karen Mothers with high Rates of Pneumococcal Nasopharyngeal Carriage", BMC Infectious Diseases, Biomed Central, London, GB, vol. 11, No. 1, p. 108, Apr. 27, 2011, (Apr. 27, 2011).

Washington, John A, "Principles of Diagnosis" In: "Medical Microbiology 4th edition", XP55285474, pp. 1-12, Jan. 1, 1996, (Jan. 1, 1996).

Notice of Reasons for Refusal for Japanese Patent Application No. 2018-506805 dated Feb. 18, 2020.

* cited by examiner

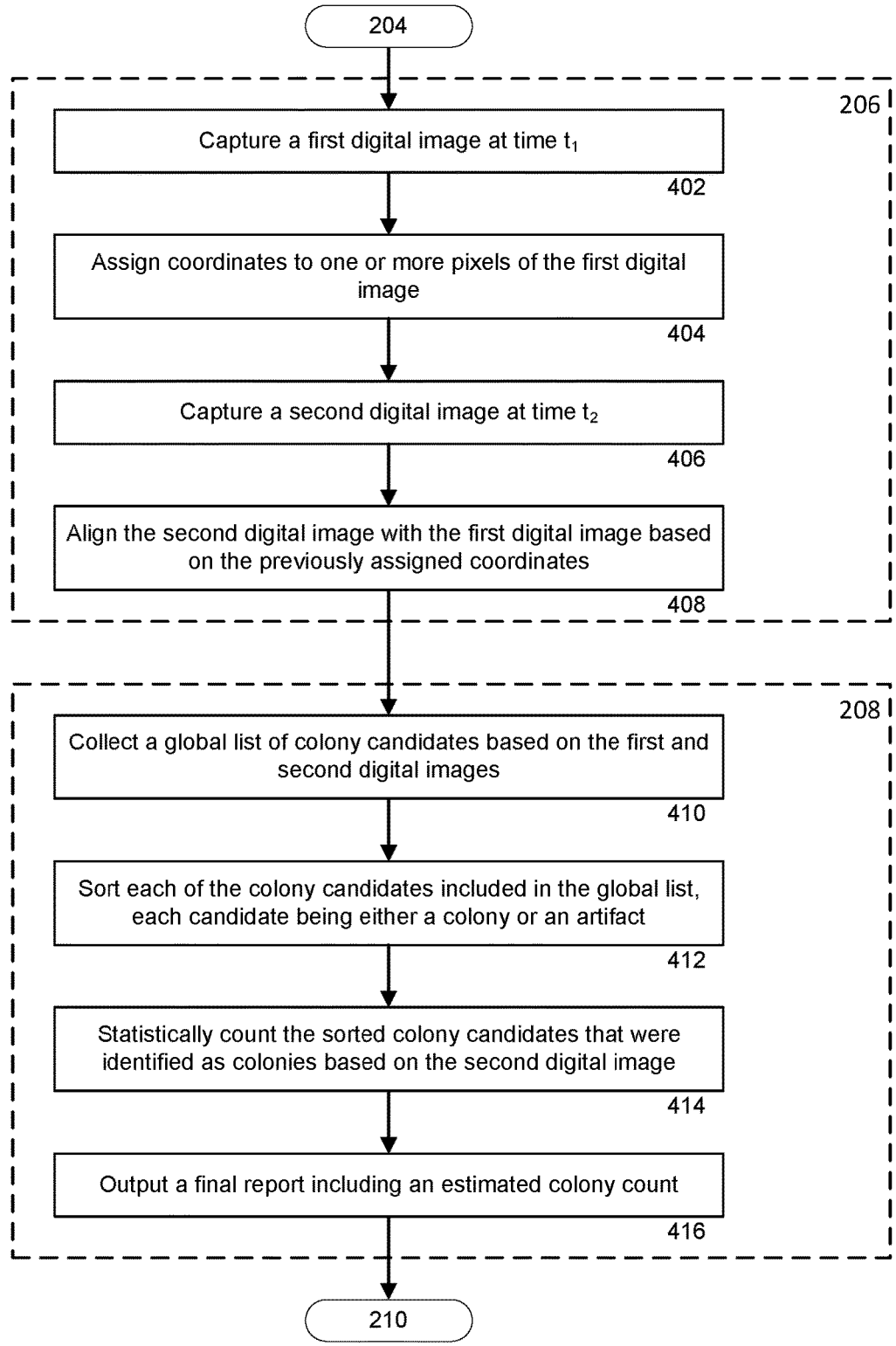

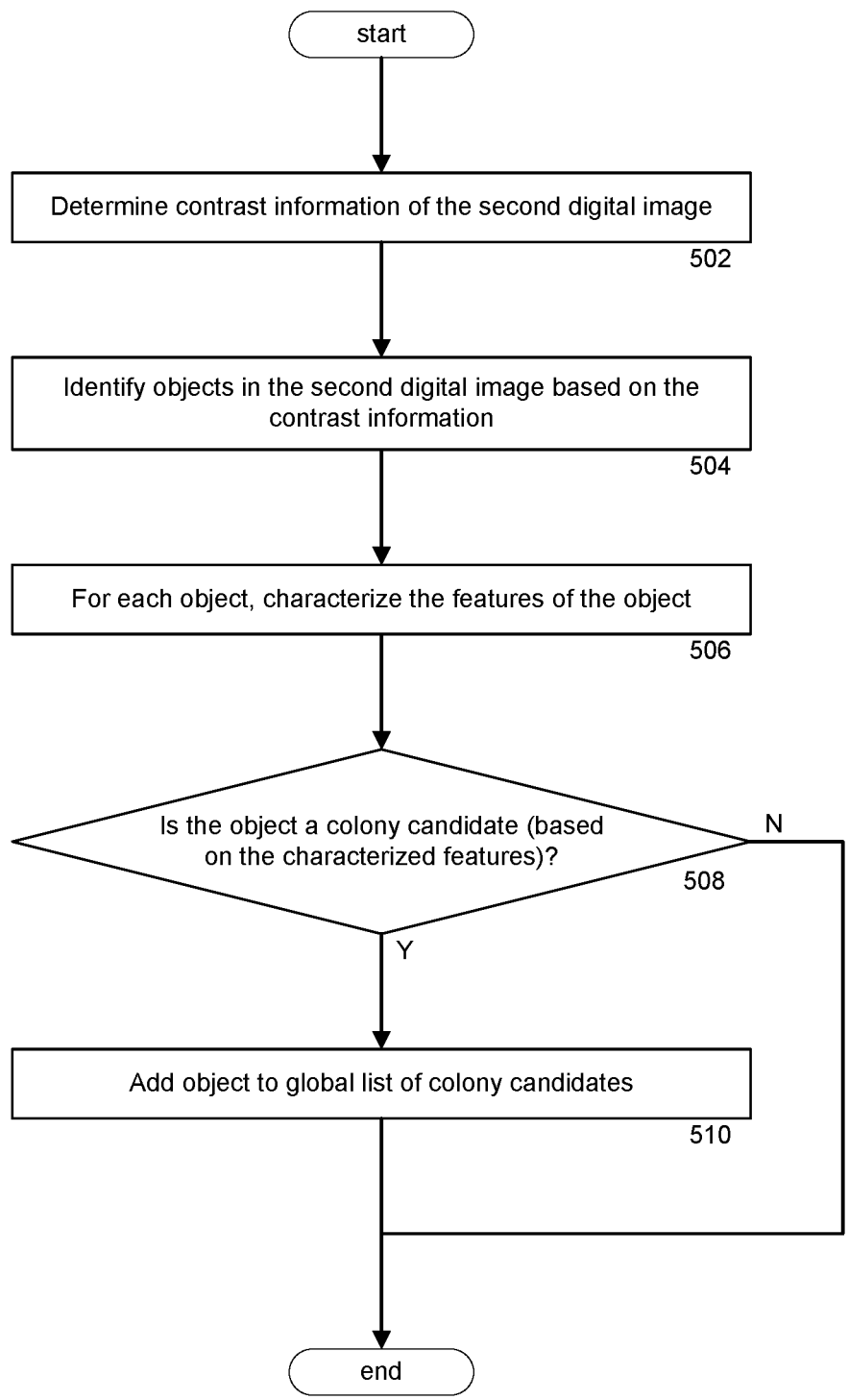
FIGURE 5    500

FIGURE 7                    700

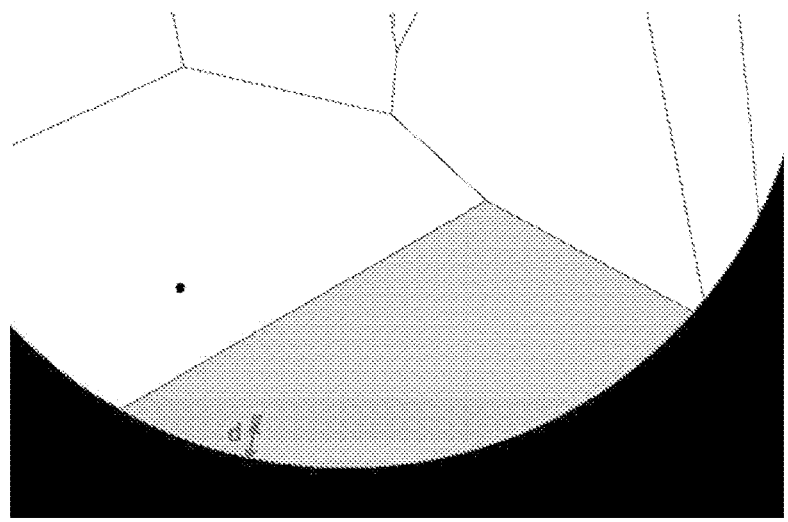
FIGURE 15A
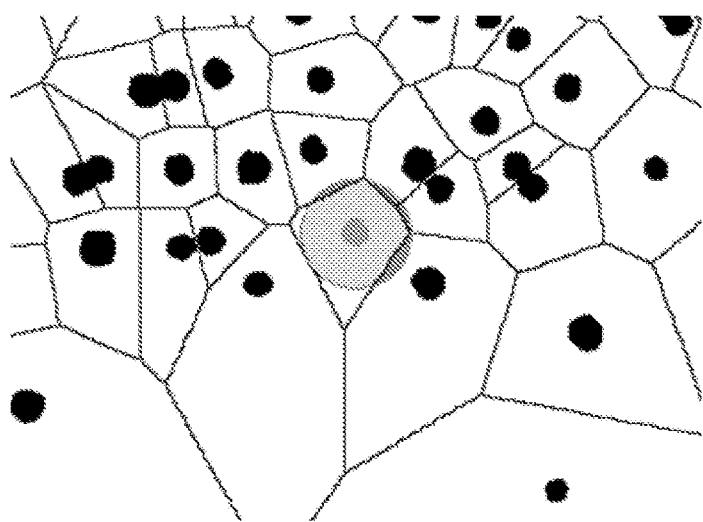
FIGURE 15B
FIGURE 15C
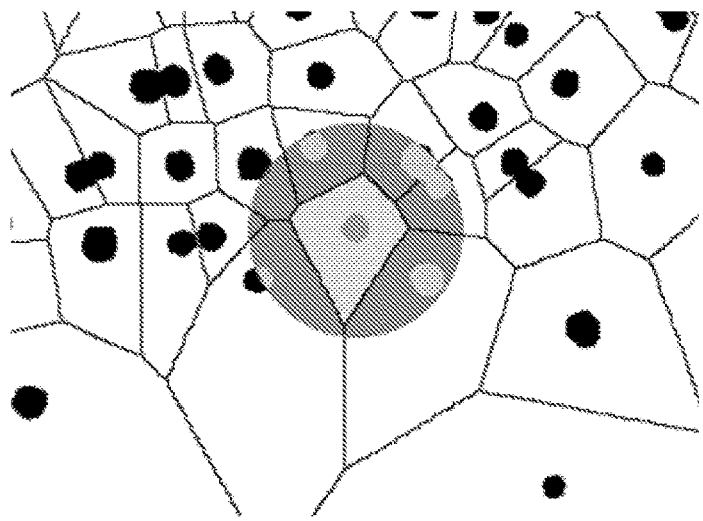

METHOD AND SYSTEM FOR AUTOMATED MICROBIAL COLONY COUNTING FROM STREAKED SAMPLE ON PLATED MEDIA

CROSS-REFERENCE TO RELATED APPLICATIONS

The present application is a national phase entry under 35 U.S.C. § 371 of International Application No. PCT/US2016/028919 filed Apr. 22, 2016 published in English, which claims priority from U.S. Provisional Application Nos. 62/151,688 filed Apr. 23, 2015, and U.S. Provisional Application No. 62/318,488, filed Apr. 5, 2016, all of which are incorporated herein by reference.

BACKGROUND OF THE INVENTION

There is increased focus on digital imagery of culture plates for detection of microbial growth. Techniques for imaging plates for detecting microbial growth are described in PCT Publication No. WO2015/114121, the entirety of which is incorporated by reference herein. Using such techniques, laboratory staff is no longer required to read plates by direct visual inspection but can use high quality digital images for plate inspection. Shifting laboratory workflow and decision-making to examination of digital images of culture plates can also improve efficiency. Images can be marked by an operator for further work-up by either the operator or another person with the appropriate skills. Additional images may also be taken and used to guide secondary processes.

Detection of colonies, colony enumeration, colony population differentiation and colony identification define the objectives for a modern microbiology imaging system. Having these objectives realized as early as possible achieves the goals of delivering results to a patient quickly and providing such results and analysis economically. Automating laboratory workflow and decision-making can improve the speed and cost at which these goals may be achieved.

Although significant progress has been made regarding imaging technologies for detecting evidence of microbial growth, it is still sought to extend such imaging technologies to support an automated workflow. Apparatus and methods for inspecting culture plates for indications of microbial growth are difficult to automate, due in part to the highly visual nature of plate inspection. In this regard, it is desirable to develop techniques that may automatically interpret culture plate images and determine the next steps to be performed (e.g., identification of colonies, susceptibility testing, etc.) based on the automated interpretation.

For example, counting colonies in a plated culture can be difficult, especially when the colonies are of different size and shape and are touching each other. These problems are exacerbated when growth has already reached confluence in some regions of the plate. For these reasons, it is preferable, if possible, to count CFUs early in the incubation process. However, time for incubation is still needed to allow for at least some growth of the colonies. Thus, on the one hand, the longer that colonies are allowed to grow, the more they begin to contrast with their background and each other, and the easier it becomes to count them. Yet, on the other hand, if the colonies are allowed to grow too long and they begin to fill the plate and/or touch one another, thereby forming confluent regions on the plate, it becomes more difficult to contrast them from one another, making counting more difficult. If one were able to detect colonies at an incubation time when the colonies were still small enough to be isolated from one another despite relatively poor contrast, or if one were able to estimate colony count even when the colonies are large enough to form confluent regions on the plate, this problem could be resolved.

BRIEF SUMMARY OF THE INVENTION

An aspect of the present disclosure is directed to an automated method for evaluating growth on plated media, comprising: providing a culture media inoculated with a biological sample; incubating the inoculated culture media; following incubation, obtaining a first image of the inoculated media at a first time ($t_1$); after further incubation, obtaining a second image of the inoculated media at a second time ($t_2$); aligning the first image with the second image, such that the coordinates of a pixel in the second image are about the same as the coordinates of a corresponding pixel in the first image; comparing image features of the second image with image features of the first image; classifying image features of the second image as colony candidates based on image feature changes from time $t_1$ to time $t_2$; for colony candidates determined to be from a common microorganism in the biological sample inoculated on the culture media, counting said colony candidates; and determining whether the number of counted colonies meets or exceeds the threshold count value stored in memory and indicative of significant growth.

In some examples, if the number of counted colonies meets or exceeds the threshold count value, the method may further comprise: identifying at least one of the colonies using matrix-assisted laser desorption ionization (MALDI); testing said at least one colony for antibacterial susceptibility; and outputting a report containing the MALDI and antibacterial susceptibility test results. A plurality of threshold count values may be stored in the memory, each threshold count value being associated with a different microorganism.

In some examples, classifying image features of the second image as colony candidates may comprise: determining contrast information of the second image, the contrast information including at least one of spatial contrast information indicating differences between pixels of the second image and temporal contrast information indicating differences between pixels of the second image and corresponding pixels of a previous image; identifying an object in the second image based on the contrast information; and obtaining one or more object features of the identified object from pixel information associated in the first and second images, wherein the object is classified as a colony candidate based on the object features. The method may further comprise, for each colony candidate, determining whether the colony candidate is a colony or an artifact based on pixel information associated with the colony candidate, wherein colony candidates that are determined to be artifacts are not counted. Determining whether a colony candidate is a colony or an artifact may further comprise determining whether the colony candidate is present in each of the first and second images and larger in the second image than the first image by a threshold growth factor, wherein a colony candidate that is present in both images and is larger in the second image by at least the threshold growth factor is classified as a colony. Determining whether a colony candidate is a colony or an artifact may further comprise, for a colony candidate that is present in the second image and not the first image: obtaining one or more object features of the identified object from the pixel information associated with the object in the second image; determining a probability that the colony candidate is a colony based on the one or more object features; and comparing the determined probability to a predefined threshold probability value, wherein, if the determined probability is greater than the predefined threshold probability value, then the colony candidate is classified as a colony. The method may further comprise: classifying (i) colony candidates that are present in both images and not larger in the second image, and (ii) colony candidates that are present in first image and not in the second image, as definite artifacts; classifying colony candidates that are present in each of the first and second images and larger in the second image by the threshold growth factor as definite colonies; and calculating an artifact probability value based on a combination of the definite artifacts and the definite colonies, wherein the determined probability that a colony candidate is a colony is further based on artifact probability.

In some examples, the object features may comprise at least one of object shape, object size, object edge, object color, color, hue, luminance and chrominance of the pixels of the object. The method may further comprise obtaining background feature information, wherein background feature information comprises media type and media color, and wherein the object is classified as a colony candidate based further on the background feature information. In some examples, aligning the first image with the second image may comprise assigning polar coordinates to pixels of each of the first and second images such that the polar coordinates of a pixel in the second image are the same as the polar coordinates of a corresponding pixel in the first image.

Another aspect of the present disclosure is directed to automated method for estimating a number of colony forming units on plated media that has been inoculated with a culture according to a predefined pattern and incubated, comprising: after incubation of the culture, obtaining a digital image of the plated media; from the digital image, identifying colony candidates in the image; linearizing the digital image according to the predefined pattern; plotting the colony candidates according to pixels of the linearized coordinates of the digital image; and estimating the number of colony forming units on the plated media based on pixels of the colony candidates in the linearized digital image.

In some examples, the plated media from which the image was obtained may have been inoculated using a magnetically controlled bead streaked along a continuous zig-zag pattern, wherein the digital image may be linearized according to the zig-zag streaking pattern with the zig-zag streaking pattern being a main axis of the linearized image. The initial bead load of the magnetically controlled bead may be estimated from the plot of colony candidates. Estimating the initial bead load may comprise: selecting a distance from origin along the main axis of the linearized image; determining a probability that a colony forming unit is released by the bead at the selected distance; and counting the number of colony forming units present in the digital image that are farther from origin along the main axis than the selected distance, wherein the estimated initial bead load is equal to the ratio between said determined probability and said counted number of colony forming units. The distance may be selected such that no confluent regions of microbial growth are present in the image at a distance farther from an origin of the linearized image than the selected distance. The method may further comprise: selecting a plurality of distances along the main axis of the linearized image; for each of the selected distances, counting the number of colony forming units present in the digital image that are farther from an origin of the linearized image along the main axis than the selected distance; and based on the counted number of colony forming units for each distance, calculating a probability that a colony forming unit is released onto the media by the bead when a point of the bead containing the colony forming unit makes contact with the media. Determining a probability that a colony forming unit is released by the bead at a given distance may be based on said calculated probability that a colony forming unit is released onto the media by the bead when a point of the bead containing the colony forming unit makes contact with the media.

In some examples, the method may further comprise: comparing the digital image to a plurality of distribution models stored in the memory, each distribution model showing an expected distribution of colony forming units across an imaged plate for a given initial bead load, and a given probability that a colony forming unit is released onto the media when contact is made with the media; and determining the initial bead load based at least in part on the compared distribution models.

In some examples the method may further comprise: selecting a distance from the origin along the main axis of the linearized image; determining a fraction of pixels at the selected distance that are associated with a colony candidate; and estimating the initial bead load based on said determined fraction.

In some examples the method may further comprise: after incubation of the culture, obtaining a plurality of digital images of the plated media, each digital image containing one or more colony candidates; identifying one digital image in which at least some of the colony candidates form a confluent region; identifying an earlier digital image in which said colony candidates that form the confluent region in the digital image have not combined to form a confluent region; and estimating the number of colony forming units in the confluent region based on the earlier digital image.

Yet another aspect of the present disclosure is directed to computer-readable memory storage medium having program instructions encoded thereon configured to cause a processor to perform a method. The method may be any of the above methods for evaluating microbial growth on plated media, or for estimating a number of colony forming units on plated media.

Yet a further aspect of the present disclosure is directed to a system for evaluating growth in a culture media inoculated with a biological sample. The system comprises an image acquisition device for capturing digital images of the culture media, memory, and one or more processors operable to execute instructions to perform a method. In some examples, the memory may store information regarding predicted amounts of microbial growth for one or more different organisms in one or more different culture media, and the method performed by the executed instructions may be any one the above described methods for evaluating microbial growth on plated media. In other examples, the memory may store information regarding a pattern for inoculating the culture media with the biological sample, and the method performed by the executed instructions may be any one the above described methods for estimating a number of colony forming units on plated media.

BRIEF DESCRIPTION OF THE DRAWINGS

FIG. 4 is a flow chart of an example routine for counting colonies according to an aspect of the disclosure.

FIG. 5 is a flow chart of an example routine for collecting a global list of colony candidates according to an aspect of the disclosure.

FIGS. 15A, 15B and 15C are graphical depictions of determinations of isolation factor according to an aspect of the disclosure.

DETAILED DESCRIPTION

The present disclosure provides apparatus and methods for identifying and analyzing microbial growth in on plated media based in at least in part on the number of identified colonies counted in one or more digital images of the plated media. Many of the methods described herein can be fully or partially automated, such as being integrated as part of a fully or partially automated laboratory workflow.

The systems described herein are capable of being implemented in optical systems for imaging microbiology samples for the identification of microbes and the detection of microbial growth of such microbes. There are many such commercially available systems, which are not described in detail herein. One example is the BD Kiestra™ ReadA Compact intelligent incubation and imaging system. Other example systems include those described in PCT Publication No. WO2015/114121 and U.S. Patent Publication 2015/0299639, the entirety of which is incorporated by reference herein. Such optical imaging platforms are well known to those skilled in the art and not described in detail herein.

Figure 1:
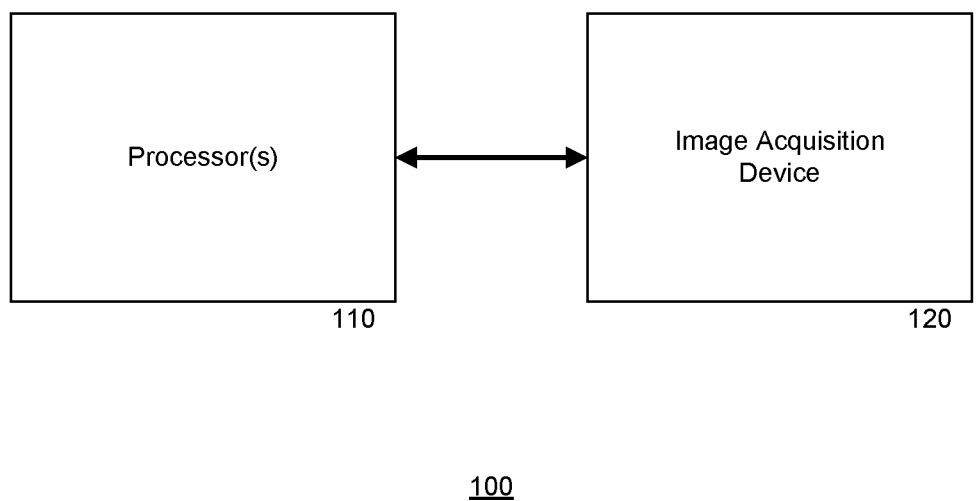
FIG. 1 is a schematic diagram of a system for imaging analyzing and testing a culture according to an aspect of the disclosure.

FIG. 1 is a schematic of a system 100 having a processing module 110 and image acquisition device 120 (e.g., camera) for providing high quality imaging of plated media. The processing module and image acquisition device may be further connected to, and thereby further interact with, other system components, such as an incubation module (not shown) for incubating the plated media to allow growth of a culture inoculated on the plated media. Such connection may be fully or partially automated using a track system that receives specimens for incubation and transports them to the incubator, and then between the incubator and image acquisition device.

The processing module 110 may instruct the other components of the system 100 to perform tasks based on the processing of various types of information. The processor 110 may be hardware that performs one or more operations. The processor 110 may be any standard processor, such as a central processing unit (CPU), or may be a dedicated processor, such as an application-specific integrated circuit (ASIC) or a field programmable gate array (FPGA). While one processor block is shown, the system 100 may also include multiple processors which may or may not operate in parallel, or other dedicated logic and memory for storing and tracking information related to the sample containers in the incubator and/or image acquisition device 120. In this regard, the processing unit may track and/or store several types of information regarding a specimen in the system 100, including but not limited to the location of the specimen in the system (incubator or image acquisition device, locations and/or orientation therein, etc.), the incubation time, pixel information of captured images, the type of sample, the type of culture media, precautionary handling information (e.g., hazardous specimens), etc. In this regard, the processor may be capable of fully or partially automating the various routines described herein. In one embodiment, instructions for performing the routines described herein may be stored on a non-transitory computer-readable medium (e.g. a software program).

Figure 2:
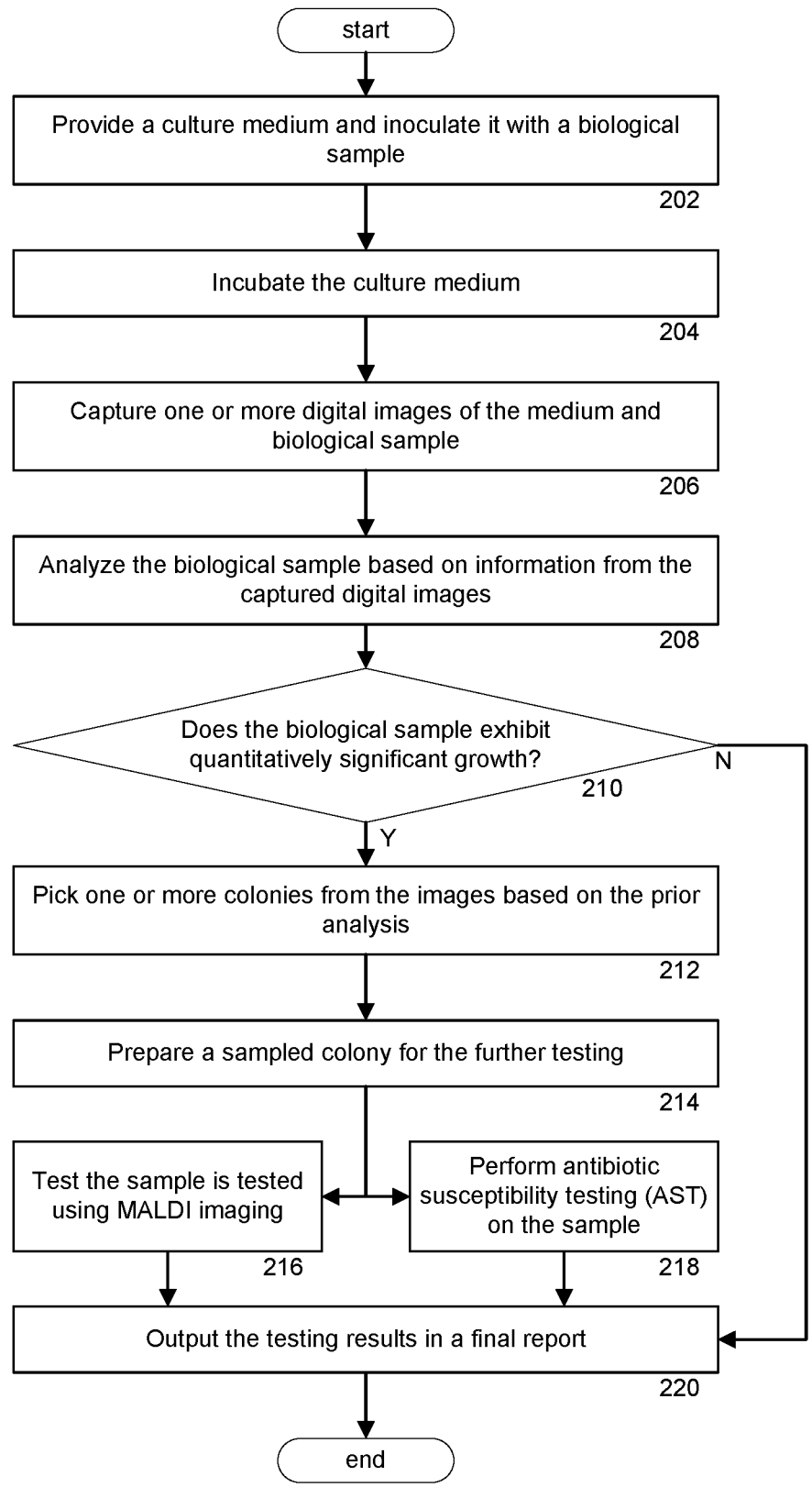
FIG. 2 is a flow chart illustrating an automated laboratory workflow routine for imaging analyzing and testing a culture according to an aspect of the disclosure.

FIG. 2 is a flow chart showing an example automated laboratory routine 200 for imaging, analyzing and, optionally, testing a culture. The routine 200 may be implemented by an automated microbiology laboratory system, such as the Kiestra™ Total Lab Automation or Kiestra™ Work Cell Automation, both manufactured by Becton, Dickenson & Co. The example systems include interconnected modules, each module configured to execute one or more steps of the routine 200.

At 202, a culture medium is provided and inoculated with a biological sample. The culture medium may be an optically transparent container, such that the biological sample may be observed in the container while illuminated from various angles. Inoculation may follow a predetermined pattern. Streaking patterns and automated methods for streaking a sample onto a plate are well known to one skilled in the art. One automated method uses magnetically controlled beads to streak sample onto the plate.

Figure 8:
FIG. 8 is an image of a streaking pattern for streaking plated media with a sample according to an aspect of the disclosure.

In some examples of the present disclosure, the bead is streaked across the plate according to a zig-zag pattern (see, e.g., FIG. 8). The starting point and end point of the zig-zag pattern may be located at opposite ends of the plate (e.g., separated by a distance about equal to the diameter of the plate). In such examples, the "main axis" of the plate may be thought of as a straight line beginning at the starting point and ending at the ending point of the zig-zag pattern.

At 204, the medium is incubated to allow for growth of the biological sample.

At 206, one or more digital images of the medium and biological sample are captured. As will be described in greater detail below, digital imaging of the medium may be performed multiple times during the incubation process (e.g., at the start of incubation, at a time in the middle of incubation, at the end of incubation) so that changes in the medium may be observed and analyzed. Imaging of the medium may involve removing the medium from the incubator. Where multiple images are taken of the medium at different times, the medium may be returned to the incubator for further incubation between imaging sessions.

At 208, the biological sample is analyzed based on information from the captured digital images. Analysis of the digital image may involve analysis of pixel information contained in the image. In some instances, pixel information may be analyzed on a pixel by pixel basis. In other instances, pixel information may be analyzed on a block by block basis. In yet further instances, pixels may be analyzed based on entire regions of pixels, whereby the pixel information of individual pixels in the region may be derived by combining information of the individual pixels, selecting sample pixels, or by using other statistical methods such as the statistical histogram operations described in greater detail below. In the present disclosure, operations that are described as being applied to "pixels" are similarly applicable to blocks or other groupings of pixels, and the term "pixel" is hereby intended to include such applications The analysis may involve determining whether growth is detected in the medium. From an image analysis perspective, growth can be detected in an image by identifying an imaged object (based on differences between the object and its adjacent surroundings) and then identifying changes in the object over time. As described in greater detail herein, these differences and changes are both forms of "contrast." In addition to detecting growth, the image analysis at 208 may further involve quantifying the amount of growth detected, identifying distinct colonies, identifying sister colonies, etc.

At 210, it is determined whether the biological sample (particularly, the identified sister colonies) exhibits quantitatively significant growth. If no growth, or an insignificant amount of growth, is found, then the routine 200 may proceed to 220, in which a final report is output. In the case of proceeding from 210 to 220, the final report will likely indicate the lack of significant growth, or report the growth of normal flora.

If it is determined that the biological sample exhibits quantitatively significant growth, then at 212, one or more colonies may be picked from the images based on the prior analysis. Picking colonies may be a fully automated process, in which each of the picked colonies is sampled and tested. Alternatively, picking colonies may be a partially automated process, in which multiple colony candidates are automatically identified and visually presented in a digital image to an operator, such that the operator may input a selection of one or more candidates for sampling and further testing. The sampling of selected or picked colonies may itself be automated by the system.

At 214, a sampled colony is prepared for the further testing, such as by plating the sample in an organism suspension. At 216, the sample is tested using matrix-assisted laser desorption ionization (MALDI) imaging to identify the type of specimen that was sampled from the original medium. At 218, the sample is also, or alternatively, subjected to antibiotic susceptibility testing (AST) to identify possible treatments for the identified specimen.

At 220, the testing results are output in a final report. The report may include the MALDI and AST results. As mentioned above, the report may also indicate a quantification of specimen growth. Thus, the automated system is capable of beginning with an inoculated culture medium and generating a final report regarding a specimen found in the culture, with little or no additional input.

In routines such as the example routine of FIG. 2, the detected and identified colonies are often referred to as Colony Forming Units (CFUs). CFUs are microscopic objects that begin as one or a few bacteria. Quantitative growth may be measured based on the number of CFUs that can be counted in the plate. However, as explained above, the number of CFUs cannot always be counted directly. For instance, the CFUs may touch or blend with one another, thereby forming confluent regions without discrete units to be counted. In such situations, the present disclosure provides for ways to estimate the colony count based on a combination of known information—such as the streaking pattern applied to the plated media, knowledge of how quickly the streaking implement is unloaded as it is streaked across the plate, standard size and growth rate for a particular type of colony being counted, etc.—and measured information collected from one or more digital images of the plate. Such estimations may be automated by the above described systems and routines.

Determining whether the estimated growth is significant may be derived from comparing the estimated colony count to a predefined threshold value. More than one threshold value may be set for a given plate and/or colony. For instance, colony growth may be affected by the medium in which the colony is being grown. Therefore, what constitutes significant growth in one medium may not constitute significant growth in another medium, and different thresholds may be set. Additionally, while testing may not be warranted for one type of bacteria until a high threshold is met, testing for particularly harmful or dangerous bacteria (e.g., Group B *streptococcus* in testing of pregnant female) may be warranted when even a low threshold value is met, in some cases even as low as one counted colony. Therefore, it should be understood that the system is capable of storing multiple threshold values and applying each of those various threshold values under the appropriate circumstances.

Over time, the bacteria grow to form a colony. The earlier in time from when the bacteria are placed in the plate, the less bacteria there is to detect and, consequently the smaller the colony and the lower that contrast to the background. Stated another way, a smaller colony size yields a smaller signal, and a smaller signal on a constant background results in smaller contrast. This is reflected by the following equation:

$$\text{Contrast} = \frac{\text{Signal} - \text{background}}{\text{Signal} + \text{background}} \quad (1)$$

Contrast can play an important role in identifying objects, such as CFUs or other artifacts, in the images. An object can be detected in an image if it is significantly different in brightness, color and/or texture from its surroundings. Once an object has been detected, the analysis may also involve identifying the type of object that has been detected. Such identifications can also rely on contrast measurements, such as the smoothness of edges of the identified object, or the uniformity (or lack of uniformity) of the color and/or brightness of the object. This contrast must be great enough to overcome the image noise (background signals) in order to be detected by the image sensor.

The human perception of contrast (governed by Weber's law) is limited. Under optimal conditions, human eyes can detect a light level difference of 1%. The quality and confidence of image measurements (e.g., brightness, color, contrast) may be characterized by a signal-to-noise ratio (SNR) of the measurements, in which an SNR value of 100 (or 40 db), independent from pixel intensities, would match human detection capabilities. Digital imaging techniques utilizing high SNR imaging information and known SNR per pixel information can allow for detection of colonies even when those colonies are not yet visible to human eyes.

In the present disclosure, contrast may be collected in at least two ways: spatially and temporally. Spatial contrast, or local contrast, quantifies the difference in color or brightness between a given region (e.g., pixel, group of adjacent pixels) and its surroundings in a single image. Temporal contrast, or time contrast, quantifies the difference in color or brightness between a given region of one image against that same region in another image taken at a different time. The formula governing temporal contrast is similar to that for spatial contrast:

$$\text{Temporal Contrast} = \frac{|\text{Signal}(t_1) - \text{Signal}(t_2)|}{\text{Signal}(t_1) + \text{Signal}(t_2)} \quad (2)$$

In which $t_2$ is a time subsequent to $t_1$. Both spatial and temporal contrasts of a given image may be used to identify objects. The identified objects may then be further tested to determine their significance (e.g., whether they are CFUs, normal flora, dust, etc.).

Figure 3A:
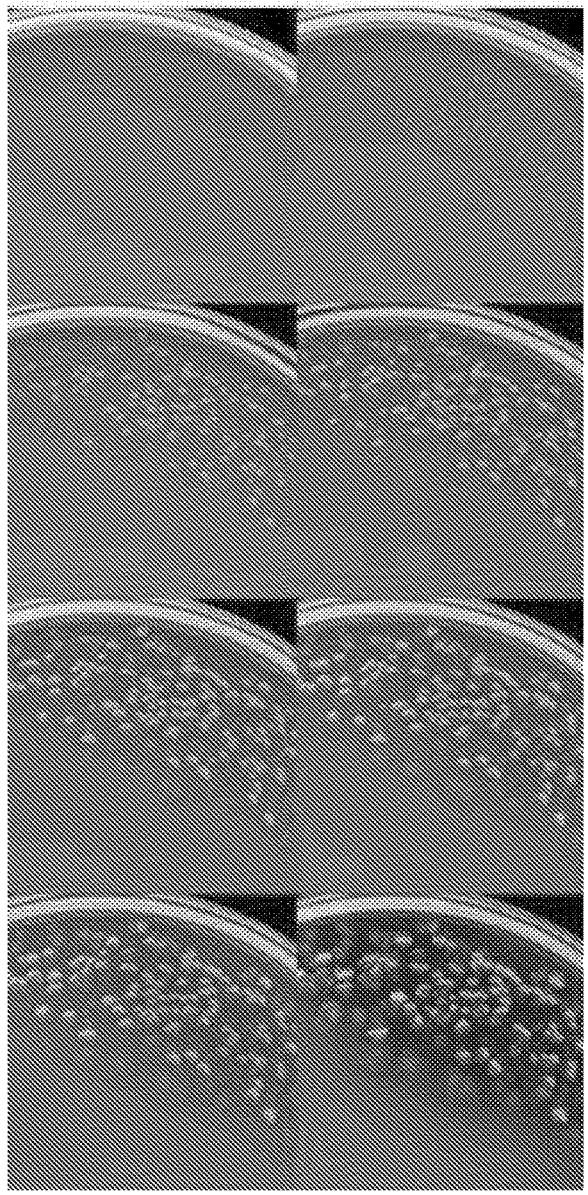
FIGS. 3A, 3B and 3C are images showing a visual representation of colony morphology as it changes over time according to an aspect of the disclosure.
Figure 3B:
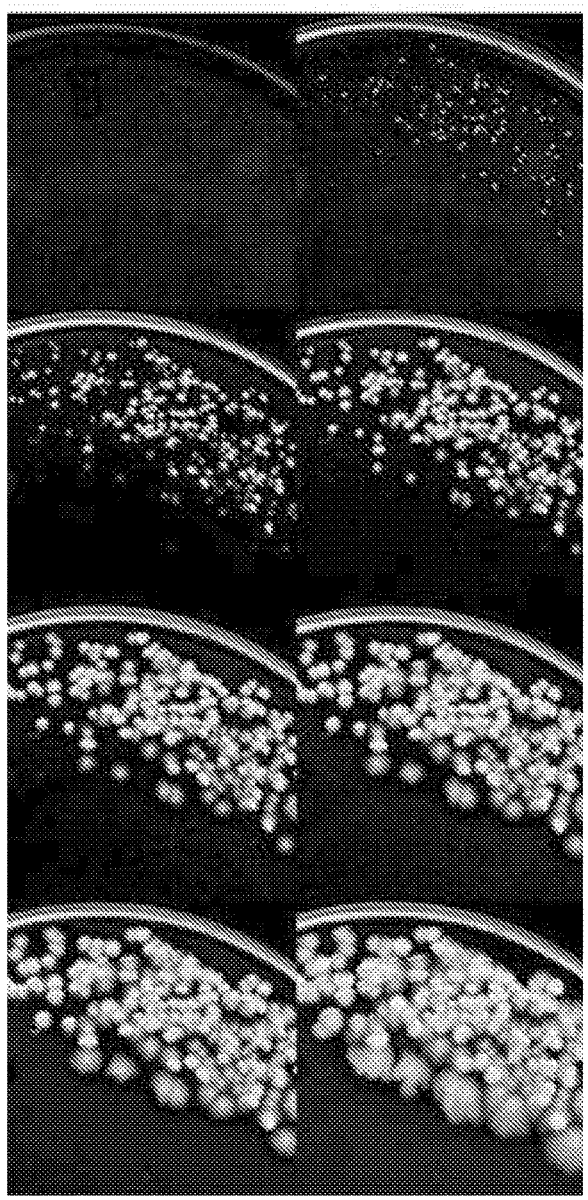
Figure 3C:
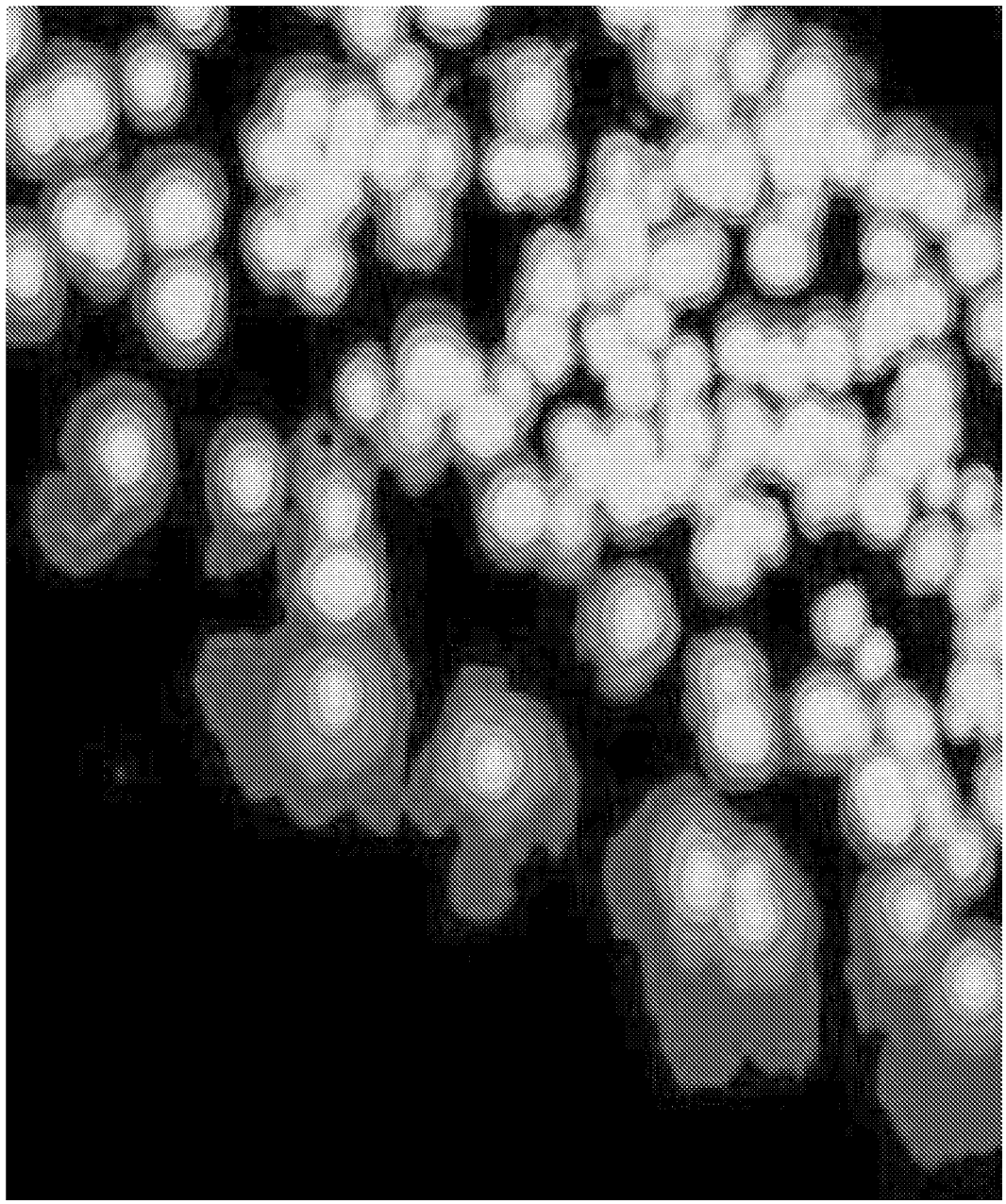

FIGS. 3A and 3B provide a visual demonstration of the effect that temporal contrast can have on an imaged sample. The images shown in FIG. 3A were captured at different points in time (left to right, top row to bottom row) showing the overall growth in the sample. While growth in noticeable in FIG. 3A, the growth is even more noticeable, and can be noticed even earlier in the sequence, from the corresponding contrast temporal images of FIG. 3B. For purposes of clarity, FIG. 3C shows a zoomed section of FIG. 3B. As can be seen in FIG. 3C, the longer a portion of a colony has been imaged, the brighter a spot it makes in the contrast image. In this way, the center of mass of each colony may be denoted by the bright center, or peak, of the colony. Thus, image data obtained over time can reveal important information about changes in colony morphology.

To maximize spatial or temporal contrast of an object against its background, the system may capture images using different incident lights on different backgrounds. For instance, any of top lighting, bottom lighting, or side lighting may be used on either a black or white background.

Figure 3D:
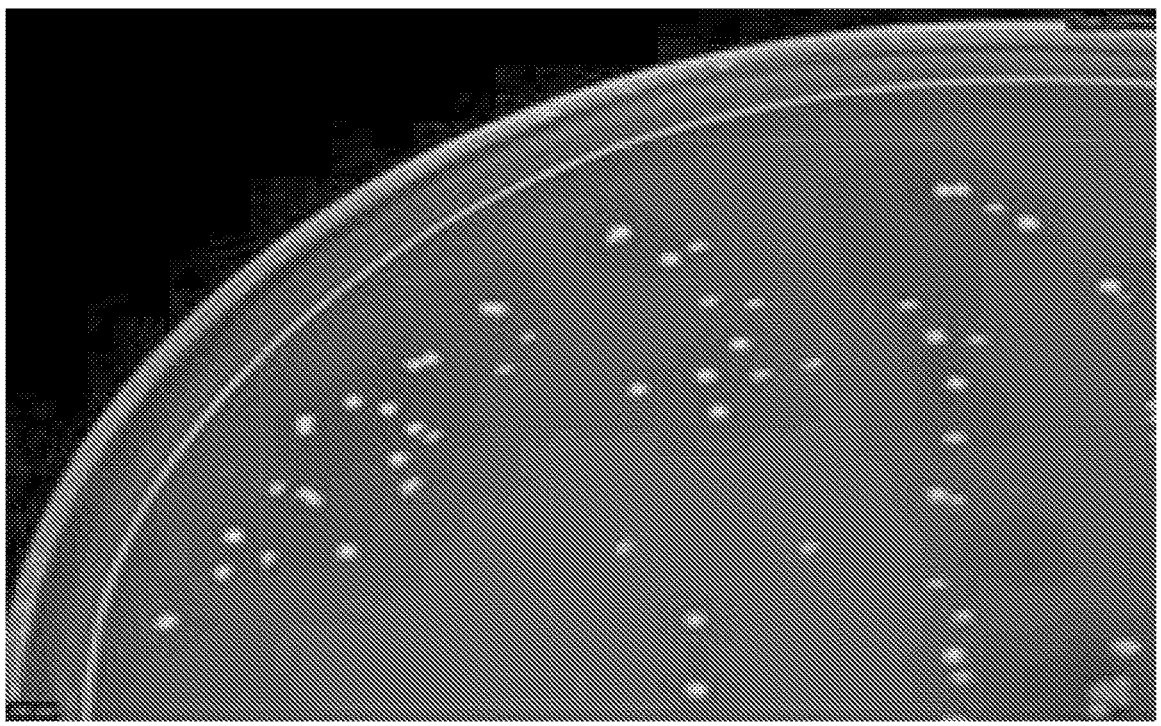
FIGS. 3D and 3E are images showing a visual representation of colonies under different illumination conditions.
Figure 3E:
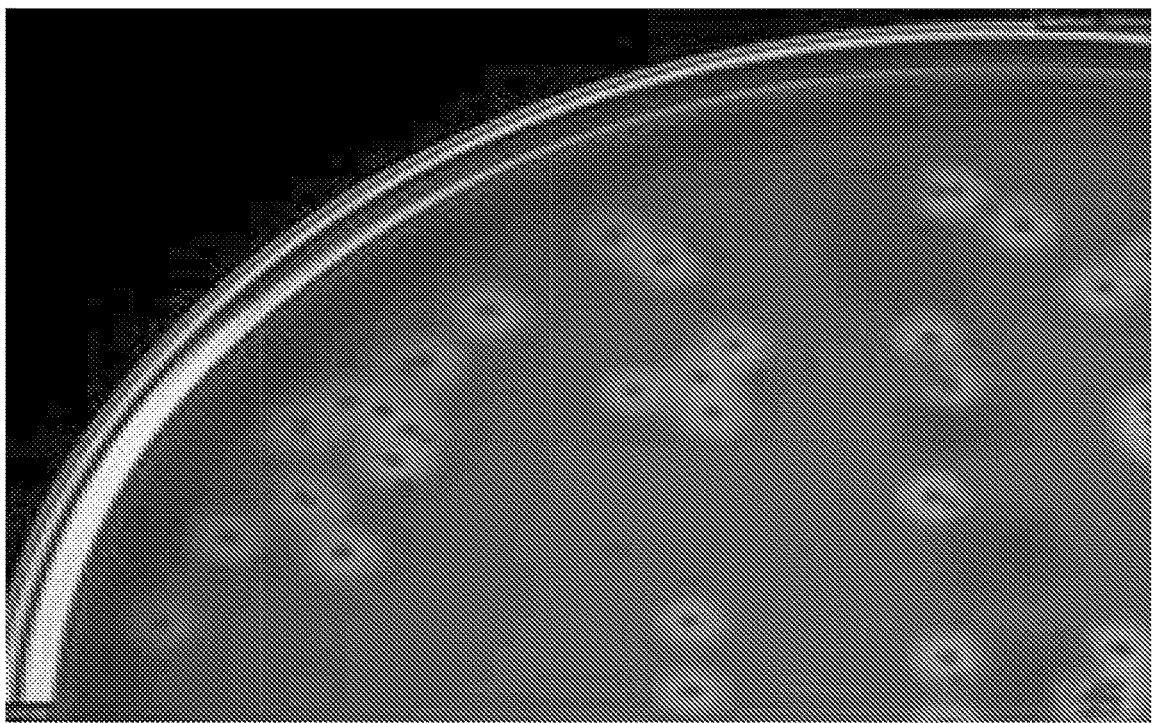

FIGS. 3D and 3E provide a visual demonstration of the effect that lighting conditions can have on an imaged sample. The image in FIG. 3D was captured using top lighting, whereas the image in FIG. 3E was captured at approximately the same time (e.g., close enough in time that no noticeable or significant growth has occurred) using bottom lighting. As can be seen, each of the images in the samples of FIGS. 3D and 3E contains several colonies, but additional information about the colonies (in this case, hemolysis) can be seen thanks to the back-lighting or bottom lighting in the image of FIG. 3E, whereas that same information is difficult to grasp in the image of FIG. 3D.

At a given point in time, multiple images may be captured under multiple illumination conditions. Images may be captured using different light sources that are spectrally different due to illumination light level, illumination angle, and/or filters deployed between the object and the sensor (e.g. red, green and blue filters). In this manner, the image acquisition conditions may be varied in terms of light source position (e.g., top, side, bottom), background (e.g., black, white, any color, any intensity), and light spectrum (e.g. red channel, green channel, blue channel). For instance, a first image may be captured using top illumination and a black background, a second image captured using side illumination and a black background, and a third image captured using bottom illumination and no background (i.e. a white background). Furthermore, specific algorithms may be used to create a set of varying image acquisition conditions in order to maximize spatial contrast using. These or other algorithms can also be useful to maximize temporal contrast by varying the image acquisition conditions according to a given sequence and/or over a span of time. Some such algorithms are described in PCT Publication No. WO2015/114121.

FIG. 4 is a flow chart showing an example routine for analyzing an imaged plate based at least in part on contrast. The routine of FIG. 4 may be thought of as an example subroutine of the routine 200 of FIG. 2, such that 206 and 208 of FIG. 2 are carried out at least in part using the routine of FIG. 4.

At 402, a first digital image is captured at time $t_1$. Time $t_1$ may be a time after the incubation process has begun, such that bacteria in the imaged plate have at least begun to form some visible colonies, but those colonies have not yet begun to touch or overlap with one another.

At 404, coordinates are assigned to one or more pixels of the first digital image. In some instances, the coordinates may be polar coordinates, having a radial coordinate extending from a center point of the imaged plate and an angular coordinate around the center point. The coordinates may be used in later steps to help align the first digital image with other digital images of the plate taken from different angles and/or at different times. In some cases, the imaged plate may have a specific landmark (e.g., an off-center dot or line), such that coordinates of the pixel(s) covering the landmark in the first image may be assigned to the pixel(s) covering the same landmark in the other images. In other cases, the image itself can be considered as a feature for future alignment.

At 406, a second digital image is captured at time $t_2$. Time $t_2$ is a time after $t_1$ at which the colonies in the imaged plate have had an opportunity to grow even more. Additional colonies that were too small to be visible at $t_1$ may also be visible at $t_2$. Also, there is a possibility that colonies at time $t_2$ have begun to touch or overlap with one another.

At 408, the second digital image is aligned with the first digital image based on the previously assigned coordinates. Aligning the images may further involve normalization and standardization of the images, for instance, using the methods and systems described in PCT Publication No. WO2015/114121.

At 410, a global list of colony candidates is collected based on the first and second digital images. The global list of colony candidates may identify any objects in the first and second digital images that may be a colony for which further testing (as in the routine of FIG. 1) may be desired.

At 412, each of the colony candidates included in the global list is sorted. Sorting the colony candidates involves identifying, for each candidate, whether the candidate is in fact an artifact or a colony. As explained in greater detail below, in some cases, it may not be possible to definitively determine whether a given candidate is an artifact or a colony. Nonetheless, a probabilistic or fuzzy determination may be made and the candidate may be sorted according to said determination.

At 414, the sorted colony candidates that were identified as colonies are counted. As explained in greater detail below, counting colonies is not always straightforward due to confluence among individual colonies. Therefore, the present disclosure provides methods and techniques for counting based on a statistical analysis of the second digital image.

At 416, a final report including an estimated colony count is outputted. The final report may optionally include additional information impacting the accuracy of the estimated colony count, such as a swarming probability among the counted colonies. Swarming refers to the confluence of colonies, thereby resulting in a swarm that the individual colonies cannot be separately identified. In some instances, the swarming probability may be reported only if it exceeds a preset threshold (e.g., 50%).

FIG. 5 is a flow chart showing an example routine 500 for collecting a global list of colony candidates. The routine of FIG. 5 may be thought of as an example subroutine of the routine 400 of FIG. 4, such that 410 of FIG. 4 is carried out at least in part using the routine of FIG. 5.

At 502, contrast information of the second digital image is determined. The contrast information may be gathered on a pixel-by-pixel basis. For example, the pixels of the second digital image may be compared with the corresponding pixels (at the same coordinates) of the first digital image to determine the presence of temporal contrast. Additionally, adjacent pixels of the second digital image may be compared with one another, or with other pixels known to be background pixels, to determine the presence of spatial contrast. Changes in pixel color and/or brightness are indicative of contrast, and the magnitude of such changes from one image to the next or from one pixel (or region of pixels) to the next, may be measured, calculated, estimated, or otherwise determined. In cases where both temporal contrast and spatial contrast is determined for a given image, an overall contrast of a given pixel of the image may be determined based on a combination (e.g., average, weighted average) of the spatial and temporal contrasts of that given pixel.

At 504, objects in the second digital image are identified based on the contrast information computed at 502. Adjacent pixels of the second digital image having similar contrast information may be considered to belong to the same object. For instance, if the difference in brightness between the adjacent pixels and their background, or between the pixels and their brightness in the first digital image, is about the same (e.g., within a predetermined threshold amount), then the pixels may be considered to belong to the same object. As an example, the system could assign a "1" to any pixel having significant contrast (e.g., over the threshold amount), and then identify a group of adjacent pixels all assigned "1" as an object. The object may be given a specific label or mask, such that pixels with the same label share certain characteristics. The label can help to differentiate the object from other objects and/or background during later processes.

Identifying objects in a digital image may involve segmenting or partitioning the digital image into multiple regions (e.g., foreground and background). The goal of segmentation is to change the image into a representation of multiple components so that it is easier to analyze the components. Image segmentation is used to locate objects of interest in images. [add cross-ref here]

At 506, the features of a given object (identified at 504) may be characterized. Characterization of an object's features may involve deriving descriptive statistics of the object (e.g., area, reflectance, size, optical density, color, plate location, etc.). The descriptive statistics may ultimately quantitatively describe certain features of a collection of information gathered about the object (e.g., from a SHQI image, from a contrast image). Such information may be evaluated as a function of species, concentrations, mixtures, time and media. However, in at least some cases, characterizing an object may begin with a collection of qualitative information regarding the object's features, whereby the qualitative information is subsequently represented quantitatively. Table 1 below provides a list of example features that may be qualitatively evaluated and subsequently converted to a quantitative representation:

TABLE 1

Qualitative Attributes of Objects, and Criteria for Quantitatively Converting the Attributes

| Number | Feature | Score | Criteria |
|---|---|---|---|
| 1 | Growth | 0 | No growth |
|   |   | 1 | Growth |
| 2 | Expected Time to Visually Observe | n/a | Record time in hours |
| 3 | Size (diameter) | 1 | <1 mm |
|   |   | 2 | >1-4 mm |
|   |   | 3 | >4 mm |
| 4 | Growth Rate ($\Delta$ diameter/2 hrs) | 1 | <1 mm |
|   |   | 2 | >1-2 mm |
|   |   | 3 | >2 mm |
| 5 | Color | 1 | grey/white |
|   |   | 2 | rose-pink |
|   |   | 3 | colorless |
|   |   | 4 | red |
|   |   | 5 | blue |
|   |   | 6 | blue-green |
|   |   | 7 | brown |
|   |   | 8 | pale yellow to yellow |
|   |   | 9 | green |
| 6 | Hemolysis | 0 | none |
|   |   | 1 | small beta(<1 mm) |
|   |   | 2 | large beta(>1 mm) |
|   |   | 3 | alpha |
| 7 | Shape | 1 | convex |
|   |   | 2 | flat |
|   |   | 3 | spread |
|   |   | 4 | Concave |
| 8 | Surface/Edge | 1 | smooth |
|   |   | 2 | rough |
|   |   | 3 | mucoid |
|   |   | 4 | feet |

Some features of an object, such as shape or the time until it is observed visually, may be measured a single time for the object as a whole. Other features may be measured several times (e.g., for each pixel, for every row of pixels having a common y-coordinate, for every column of pixels having a common x-coordinate, for every ray of pixels having a common angular coordinate, for a circle of pixels having a common radial coordinate) and then combined, for instance using a histogram, into a single measurement. For example, color may be measured for each pixel, growth rate or size for every row, column, ray or circle of pixels, and so on.

At 508, it is determined whether the object is a colony candidate based on the characterized features. The colony candidate determination may involve inputting the quantitative features (e.g., the scores shown in Table 1, above), or a subset thereof, into a classifier. The classifier may include a confusion matrix for implementing a supervised machine learning algorithm, or a matching matrix for implementing an unsupervised machine learning algorithm, to evaluate the object. Supervised learning may be preferred in cases where an object is to be discriminated from a limited set (e.g., two or three) of possible organisms (in which case the algorithm could be trained on a relatively limited set of training data). By contrast, unsupervised learning may be preferred in cases where an object is to be discriminated from an entire database of possible organisms, in which case it would be difficult to provide comprehensive—or even sufficient—training data. In the case of either confusion or a matching matrix, differentiation could be measured numerically on a range. For instance, for a given pair of objects, a "0" could mean the two objects should be discriminated from each other, whereas a "1" could mean that the objects are difficult to differentiate one from the other.

If at 508 the object is determined to be a colony candidate, then at 510, it is added to the global list of colony candidates. Otherwise, routine 500 ends (and may continue with 412 of routine 400) without adding the object to the global list.

Additional routines and subroutines for identifying colony candidates based on contrast information of digital images is discussed in the commonly owned and copending application titled "COLONY CONTRAST GATHERING," the disclosure of which is incorporated by reference in its entirety.

Figure 6:
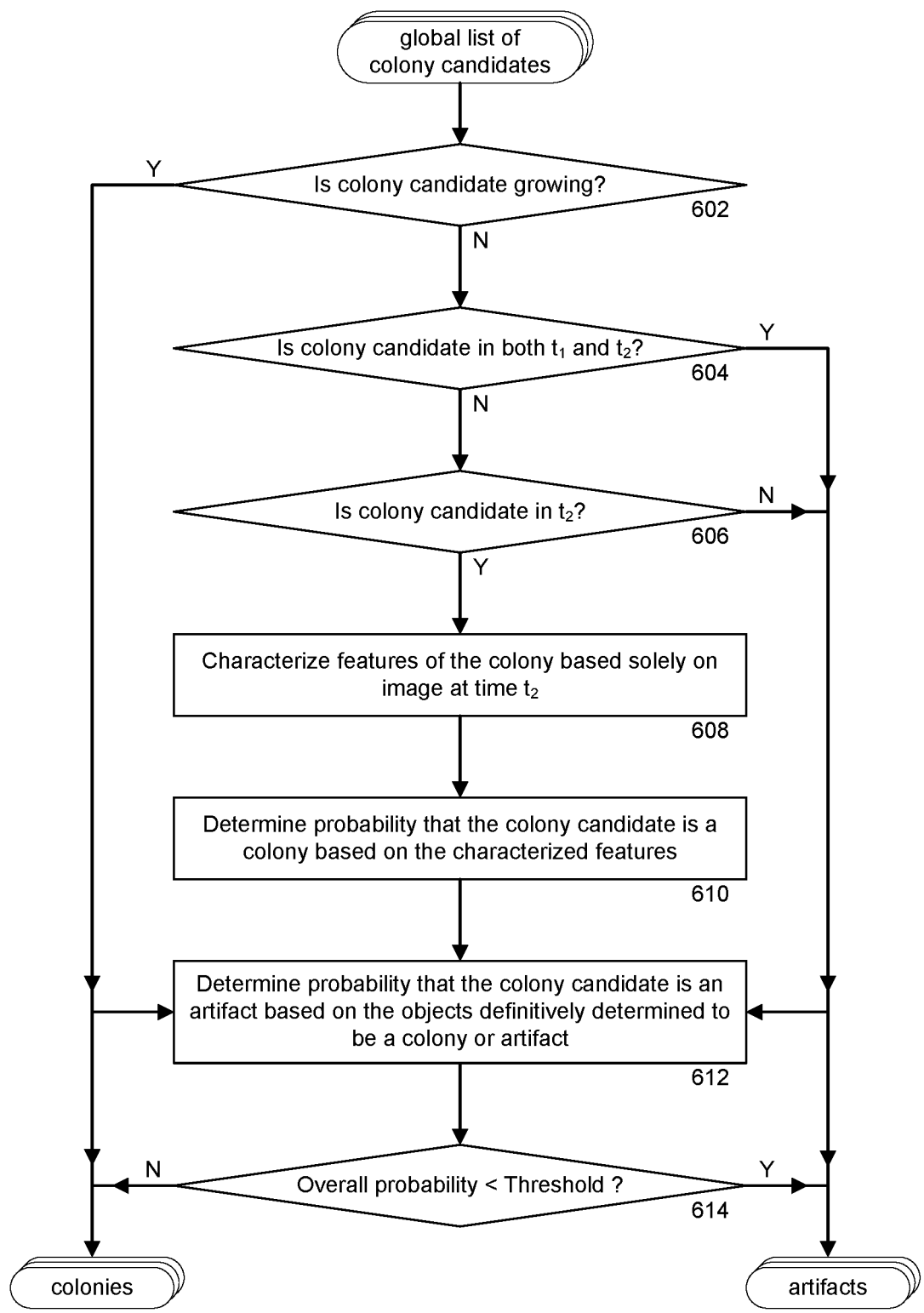
FIG. 6 is a flow chart of an example routine for sorting colony candidates according to an aspect of the disclosure.

FIG. 6 is a flow chart showing an example routine 600 for sorting the colony candidates. The routine of FIG. 6 may be thought of as an example subroutine of the routine 400 of FIG. 4, such that 412 of FIG. 4 is carried out at least in part using the routine of FIG. 6. As a subroutine of FIG. 4, routine 600 may be applied iteratively to each of the colony candidates appearing on the global list.

At 602, it is determined whether the colony candidate is growing. Growth may be indicated by (a) the colony candidate's presence in both the first and second digital images, and (b) the colony candidate's size being significantly larger in the second digital image than in the first digital image. Whether a change in size is considered significant may be determined by comparing the change in size to a predetermined growth threshold, whereby changes that meet or exceed the growth threshold are considered significant.

If the colony candidate is determined to be growing, then the colony candidate is validated and identified as a colony. Otherwise, routine 600 continues at 604, in which it is determined whether the colony candidate is present in both the first and second digital images.

If the colony candidate is determined to be present in both images (meaning that there was no significant growth between the two images), then the colony candidate is identified as an artifact. Otherwise, routine 600 continues at 606, in which it is determined whether the colony candidate is present in the second digital image.

If the colony candidate is not present in the second image (meaning that it was only present in the first image and then disappeared), then the colony candidate is identified as an artifact (e.g., a piece of dust that was likely blown off the plate between $t_1$ and $t_2$). Otherwise, further analysis is performed to determine whether the colony candidate is a colony that simply had not grown enough to be visible at time $t_1$, or an artifact such as a piece of dust that blew onto the plate between times $t_1$ and $t_2$.

At 608, given the knowledge that the colony candidate does not appear in the first digital image, features of the colony candidate are characterized based solely on information from the second digital image. The characterization may rely on static features, such as color, size, shape and surface (described above in connection with step 506 of FIG. 5).

At 610, an overall probability that the colony candidate is in fact a colony is determined based at least in part on the characterization. For instance, the characterized features of an object may be compared to features of an expected colony type (i.e., the colony type included in the global list and being counted in FIG. 6). In one embodiment, the comparison is executed in the same manner as in step 508 of FIG. 5, such that a "0" would mean the object is the expected colony type, whereas a "1" would mean that the object is not the expected colony type, and a number in between "0" and "1" would indicate a probability of the object being the expected colony type, also referred to as a colony probability.

In some instances, the colony probability may be the overall probability of 610. Alternatively, the determination at 610 may be further based on information gathered about artifacts in the image. Such information may include an artifact probability, which gauges the likelihood of objects in the image being artifacts. In the example of FIG. 6, objects that are definitely determined to be artifacts (e.g., no growth between $t_1$ and $t_2$, presence only in $t_1$ and not $t_2$) or colonies (e.g., significant growth between $t_1$ and $t_2$) are provided as an input at 612 in order to determine the artifact probability. The artifact probability of 612 is then combined with the colony probability to yield the overall probability. In one embodiment, the colony probability and artifact probability are combined according to the following equation:

$$P(\text{overall}) = P(\text{colony}) \times (1 - P(\text{artifact})) \quad (3)$$

At 614, the overall probability is compared to a predetermined threshold (e.g., 50%). If the overall probability meets or exceeds the threshold, then the colony candidate is identified as a colony. Otherwise, the colony candidate is identified as an artifact.

While the routines of FIGS. 5 and 6 are useful for classifying identified colonies, those routines do not ensure that each colony is an individual colony and not a confluence of multiple colonies. Therefore, the colony candidates that are identified as colonies cannot necessarily be counted as discrete elements, but rather counted using estimation techniques.

Figure 7:
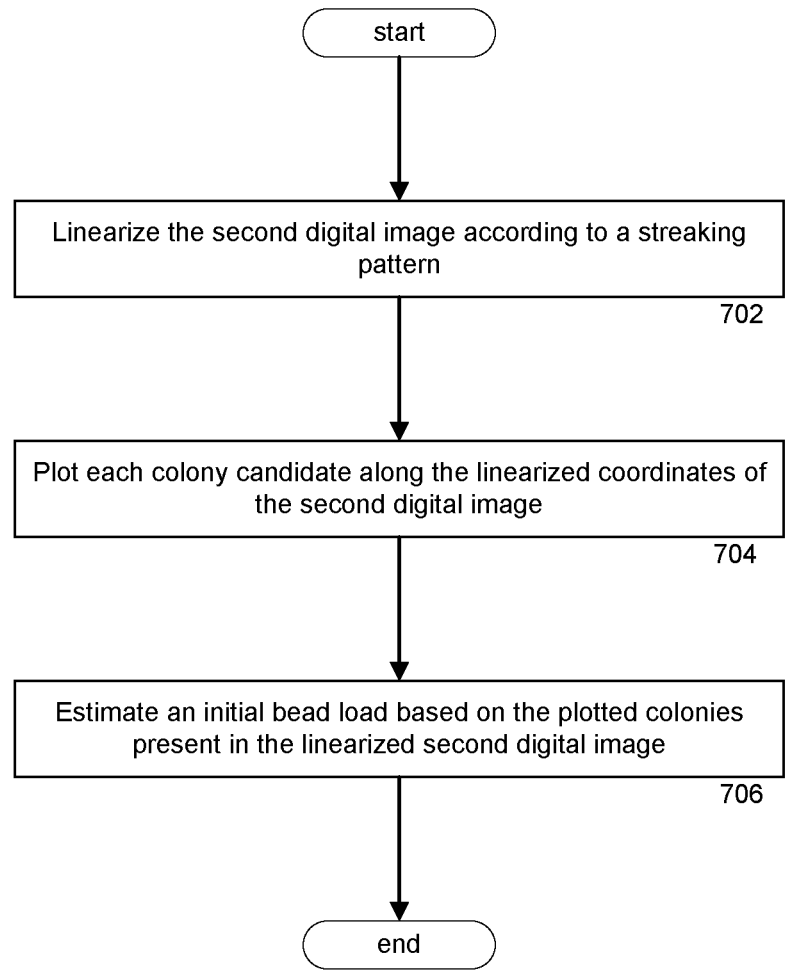
FIG. 7 is a flow chart of an example routine for counting colonies based on statistical analysis according to an aspect of the disclosure.

FIG. 7 is a flow chart showing an example routine 700 for counting colonies based on statistical analysis. The routine of FIG. 7 may be thought of as an example subroutine of the routine 400 of FIG. 4, such that 414 of FIG. 4 is carried out at least in part using the routine of FIG. 7. The routine of FIG. 7 presumed use of a magnetically controlled bead to streak colonies onto the imaged plate according to a predetermined streaking pattern. Those skilled in the art should understand that the underlying concepts of the routine of FIG. 7 may be adapted for various streaking media, techniques and patterns, other than those described below.

At 702, the second digital image is linearized according to a streaking pattern along which the imaged plate is streaked by the magnetically controlled bead. To illustrate the streaking pattern, FIG. 8 shows an image a sample growing in a plated media. The image is digitally overlaid with a zig-zag pattern beginning toward the bottom right of the image and ending toward the top left. The zig-zag pattern indicates the streaking pattern of the magnetically controlled bead used to streak the media.

For purposes of clarity, linearizing the digital image may be thought of as plotting the pixels of the zig-zag pattern along an x-axis of the linearized image, such that the zig-zag pattern is unfolded into a straight line along the x-axis. For each pixel of the digital image that does not directly overlay the zig-zag pattern, and the pixel may be associated with the closest part of the zig-zag pattern to the pixel (e.g., along a y-axis of the linearized image). The linearize image is useful for indicating the density gradient of colonies deposited onto the media by the bead as the bead moves along the streaking pattern over time.

Figure 9B:
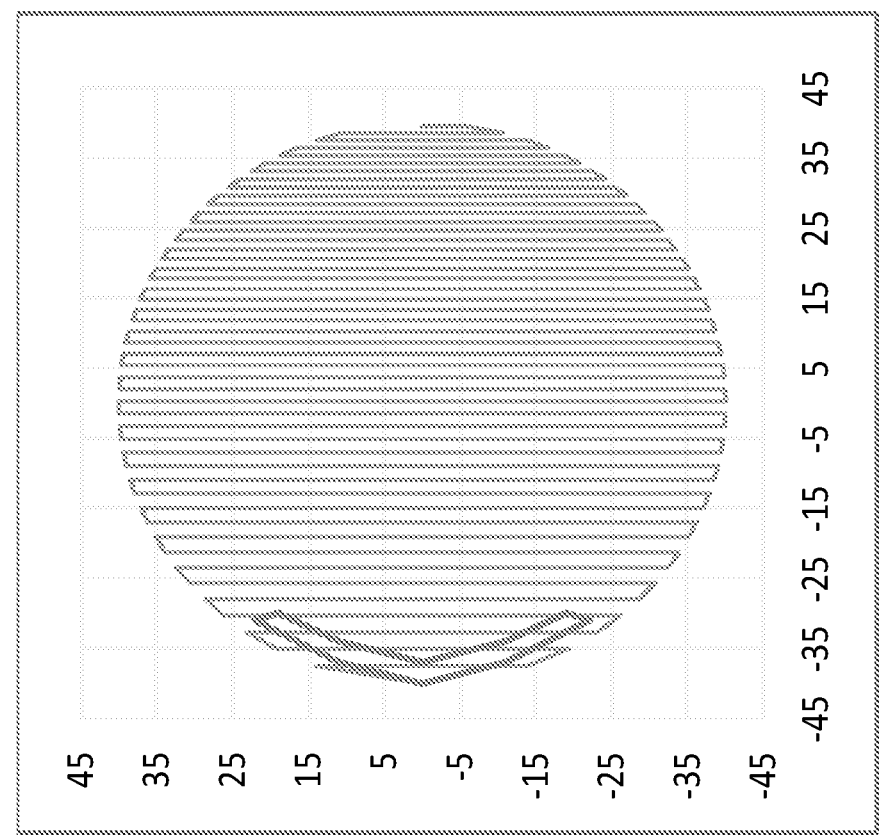
FIG. 9B is a graphical representation of the streaking pattern shown in FIG. 8.
Figure 9A:
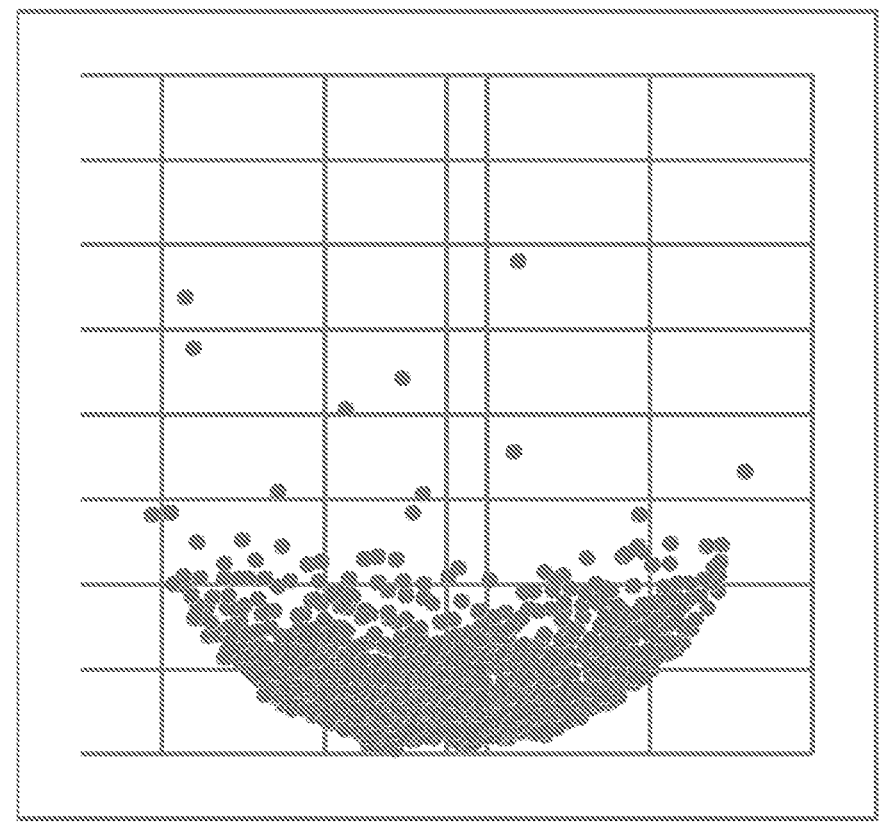
FIG. 9A is a graphical representation of an image of identified colony candidates according to an aspect of the disclosure.

At 704, each colony candidate is plotted along the linearized coordinates of the second digital image. In other words, the density gradient of colonies deposited onto the media is assessed using the linearized image. FIG. 9A is a graphical representation of previously identified colony candidates (e.g., from the routine 500 of FIG. 5). FIG. 9B is a graphical representation of the zig-zag pattern. By overlaying the representations of FIGS. 9A and 9B, the distance of every colony candidate along the zigzag pattern from the pattern origin (leftmost end of the image) can be computed.

At 706, an initial bead load (a concentration, measured in CFUs per milliliter) is estimated based on the plotted colonies present in the linearized second digital image. Calculations for estimating initial bead load are presented herein for a bead streaking a path having a width (W) measured in mm (also referred to as the "contact width") and having a surface area (SA) of "SA" measured in mm$^2$.

As an initial point, it is noted that for a given point on the surface of the bead, on average that point will come into contact with the plate once for every "B" mm that the bead travels along the zig-zag pattern, where:

$$B = \frac{SA}{W} \quad (4)$$

If it is assumed that the given point is loaded with a colony forming unit (CFU), then the probability of the CFU being released onto the media ($P_R$) when the contact between the given point and the media is made may be characterized as a number between 0 and 1.

By the time the bead has progressed a distance x (measured in mm) along the streaking path, the probability that a CFU at the given point has been released ($P_{NR}(x)$) is given according to the following relationship:

(5)

$$P_{NR}(x) = (1 - P_R)^{x/B} \quad (18)$$

As the bead progress and releases CFUs, the CFU load present on the bead decreases. The total CFU load present on the bead at the given time at which the bead has so far travelled distance x along the streaking pattern may be characterized as K(x). K(x) can further be expressed as a function of the initial bead load $K_0$ (i.e., the CFU load of the bead before the streaking pattern began and, thereby, before any CFUs were released):

(6)

$$K(x) = K_0 \times P_{NR}(x) = K_0 \times (1 - P_R)^{x/B} \quad (19)$$

K(x) can also be estimated based on the linearized digital image. Specially, it may be assumed that all of the CFUs initially loaded onto the bead will be released onto the media by completion of the streaking pattern, therefore, the remaining load on the bead at any given distance x may be characterized as $\Sigma_x^\infty$ CFU, the number of colonies shown in the digital image past distance x. (In reality the upper limit of the sum should be the length of the streaking pattern, not ∞, but given the assumption that all CFUs are released by the end of the streaking pattern, an upper limit of infinity is equally acceptable.)

Using the estimate of K(x), that estimate can be plugged into the above equations to solve for initial bead load $K_0$. In fact, for any given distance x that K(x) can be estimated (e.g., x1, x2, x3, etc.), $K_0$ can be also be independently solved for, as shown by the following equations:

$$K_0 = \frac{\sum_{x1}^\infty CFU}{(1 - P_R)^{x1/B}} = \frac{\sum_{x2}^\infty CFU}{(1 - P_R)^{x2/B}} = \frac{\sum_{x3}^\infty CFU}{(1 - P_R)^{x3/B}} = \ldots \quad (7)$$

While in the above example the release probability $P_R$ was assumed, it is further noted that the above series of equations can also be used to solve for $P_R$ using two or more of the estimations of $K(x) = \Sigma_x^\infty$ CFU along the streaking pattern. The following is an example of a formula for solving for $P_R$ using the estimated K(x) values for distances x1 and x2.

$$P_R = 1 - e^{\frac{35.5}{(x2-x1)} \times ln\left(\frac{\sum_{x2}^\infty CFU}{\sum_{x1}^\infty CFU}\right)} \quad (8)$$

Having solved for $P_R$, $K_0$ may be estimated using the determined values for $P_R$ and K(x), according to the following equation:

(22)

$$K_0 = \frac{K(x)}{(1 - P_R)^{x/B}} \quad (9)$$

It should be noted that the more values of K(x) that are estimated, the more precise the estimates of $P_R$ and $K_0$ may become. Therefore, while the above example uses only x1 and x2 to estimate $K_0$, other examples may use additional distances (e.g., x3).

Alternatively, $P_R$ may be a predetermined value based on known features of the colony, media, bead, or any combination thereof, in which case $K_0$ may be estimated based on the estimated value of K(x) at a single given distance x.

Distribution Model

Figure 10A:
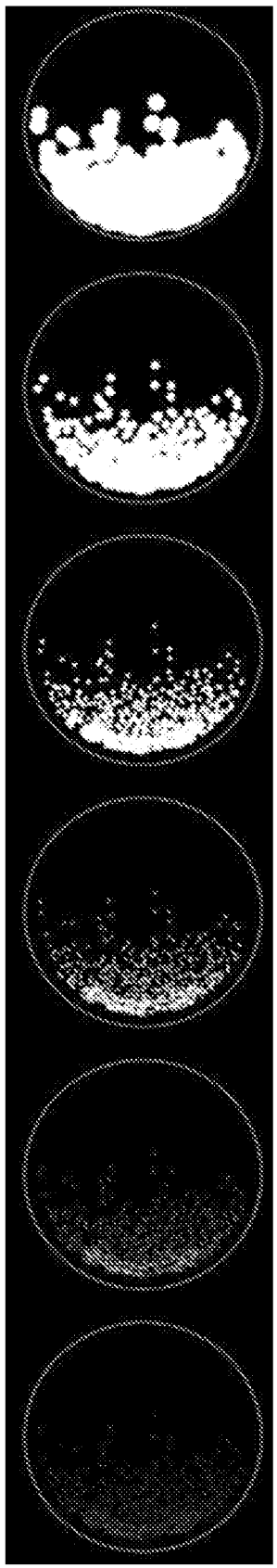
FIGS. 10A and 10B are graphical representations for colony forming unit (CFU) distribution models according to an aspect of the disclosure.
Figure 10B:
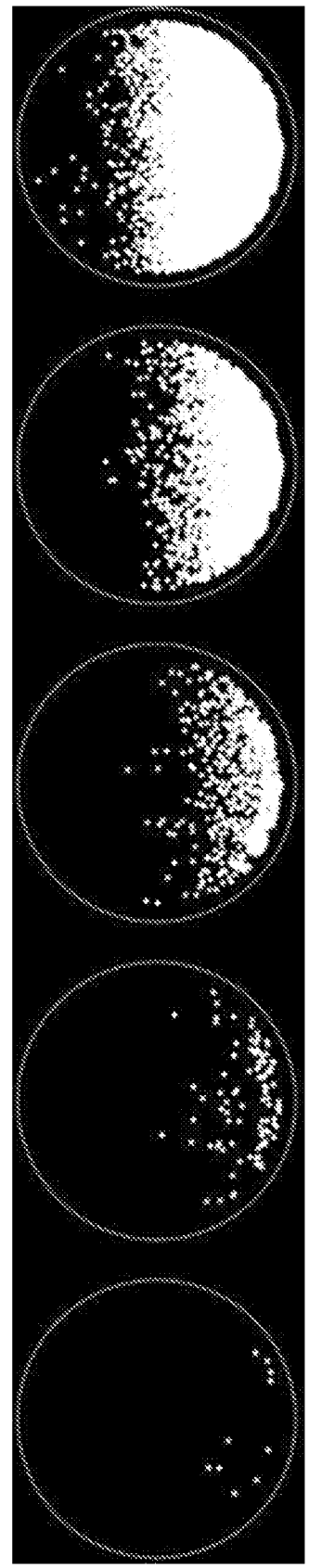

In addition to the above calculations, colonies on the imaged plate may be estimated based on a comparison between the digital image and a distribution model. FIGS. 10A and 10B illustrate CFU distribution models based on a given bead release probability ($P_R$) Each of FIGS. 10A and 10B show distributions of CFUs for varying initial bead loads (ranging from a small initial load, e.g., $10^2$, at the leftmost image to a large initial bead load, e.g., $10^5$, at the rightmost image). The distribution models may also be modified to account for variables such as release probability and colony size. In the examples of FIGS. 10A and 10B, the release probability is set to 0.14. In FIG. 10A, the colony size is set to 1.66 mm in diameter. In FIG. 10B, the colony size is set to a smaller diameter. Accordingly, with knowledge of the release probability and colony size for a given sample, distribution models may be used to estimate initial bead load for an image having a similar appearance in distribution.

Confluence Ratio

Confluence ratio can also be utilized in order to improve the colony count estimation. Confluence ratio is the fraction of pixels, at a given distance along the main axis of the plate, that are associated with a colony candidate. Confluence ratio may be characterized according to the following:

$$Conf_{a\%} = x \text{ such that } \frac{\sum_{x,y=-R}^{x,y=R} CFU \text{ candidate pixel}}{\sum_{x,y=-R}^{x,y=R} \text{Media pixel}} = a\% \quad (10)$$

Figure 11B:
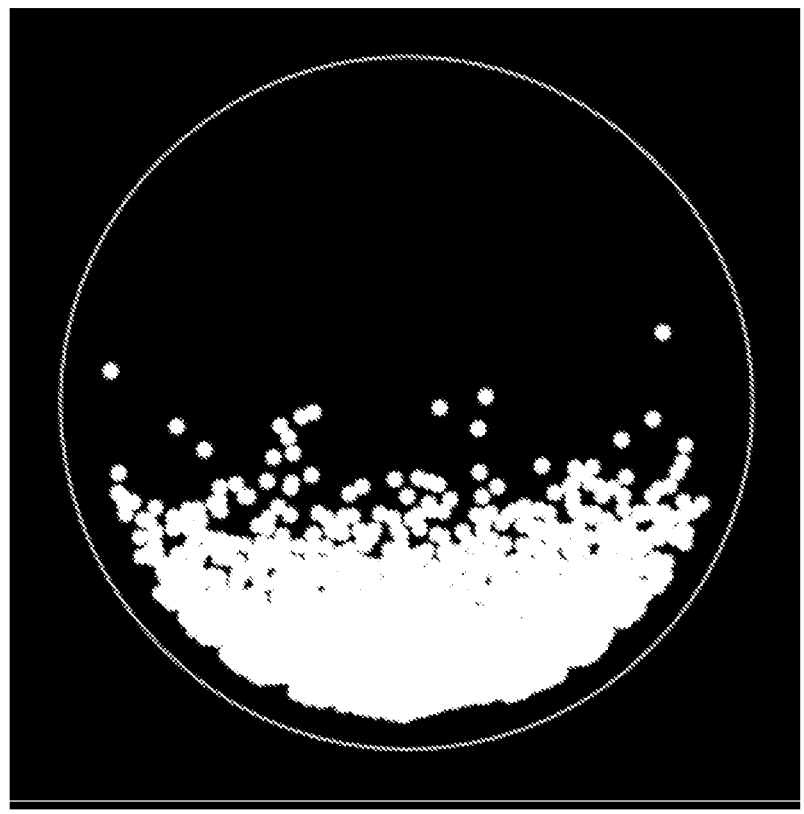
FIG. 11B is a graphical representation of a colony growth simulation according to an aspect of the disclosure.
Figure 11A:
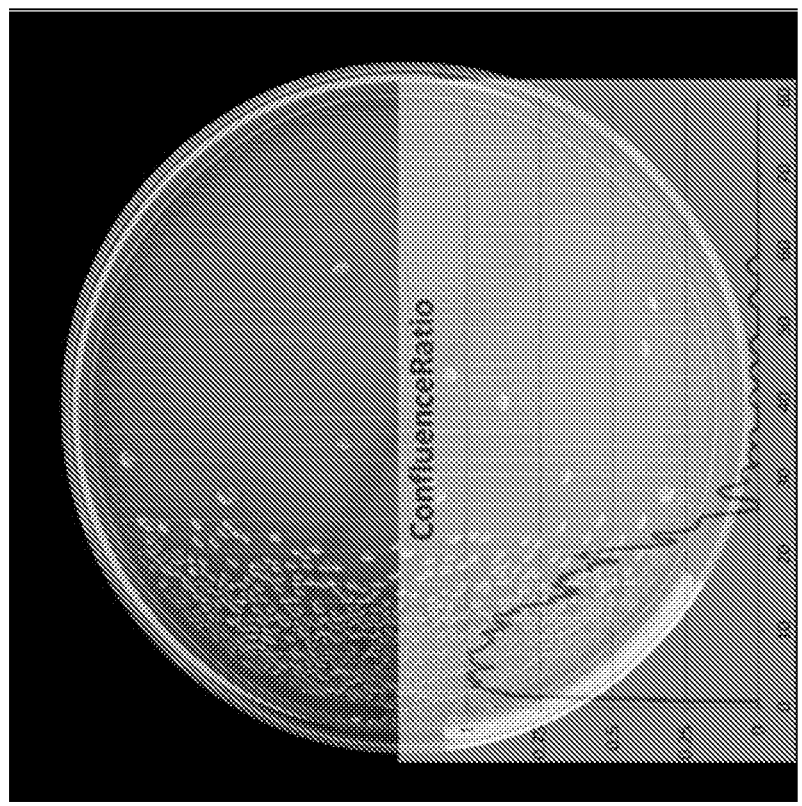
FIG. 11A is a graphical representation of confluence ratio along a main axis of the plate shown in FIG. 8 according to an aspect of the disclosure.

FIG. 11A illustrates the confluence ratio of a plate as measured along the main axis of the streaking pattern from origin to end. In the example of FIG. 11A, the expected CFUs on the plate were 4800. FIG. 11B depicts the result of a simulation with a 4800 CFU initial load having a release probability of 0.185 and a colony size of about 2 mm in diameter. As can be seen in the present example, confluence shown in the plate of FIG. 11A and the simulation of FIG. 11B are fairly similar to one another.

Confluence ratio can also be used to identify a tangent line zero crossing, which is the point along the main axis at which the confluent region mainly or mostly ends (e.g., more discrete colonies than confluent colonies, confluent regions make up less than 50% of the pixels along a line running through said point and perpendicular to the main axis, etc.).

Figure 12:
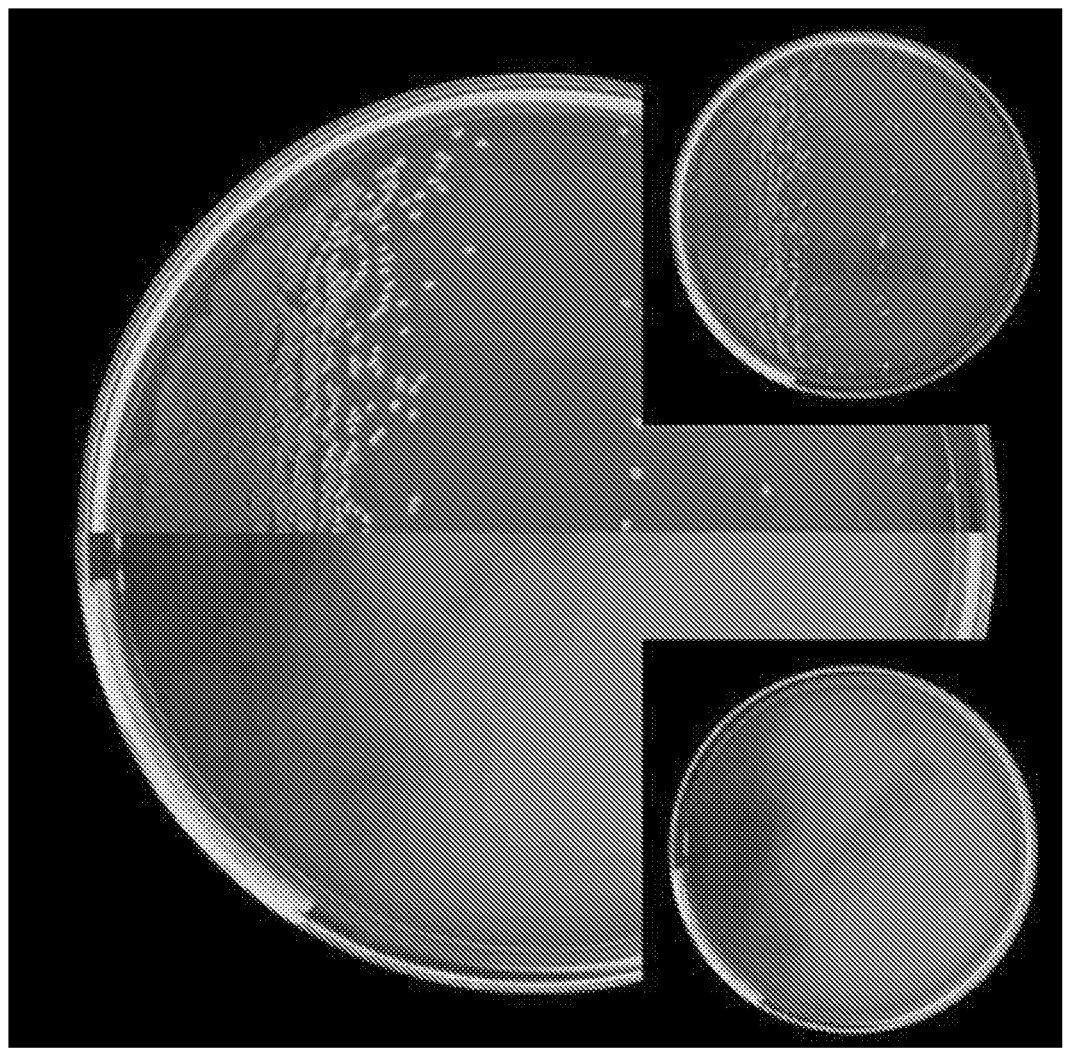
FIG. 12 is a side-to side depiction of two images of plate media with colony growth.

It should be recognized from the above examples that the expected confluence ratio along the main axis of a plate depends largely on the initial load (CFU/ml), the size of isolated colonies at the given time that the plate is being imaged, and the given incubation time. To highlight these factors, FIG. 12 is a side-to side depiction of two plates having similar confluence ratios but significantly different CFU loads. The top plate contains a total of about 39,500 CFUs of *Staphylococcus aureus*, whereas the bottom plate contains about 305 CFUs of *Pseudomonas aeruginosa*. Notably the confluence ratio of these plates is about the same as the plate shown in FIG. 11A (which contains about 4,800 CFUs of *Serratia marcescens* on a blood agar media after 18 hours of incubation). [INVENTORS: What is a "tangent line zero crossing" method?]

Time-Series Analysis

Another way of estimating CFU content within a confluence region is to performing time-series analysis by splitting the confluent region into discrete colonies using past images. As stated above, colonies that have confluence at a given time may still be discrete and individually countable at an earlier time. Therefore, an analysis may be conducted using images of the confluent region from earlier incubation times when confluence conditions were not yet met for at least some of the colonies (e.g., running segmentation routines, building a Voronoï diagram, etc.). This analysis could then be used to keep tracks of ongoing changes over time to help maintain identification of discrete colonies at subsequent times.

Figure 13:
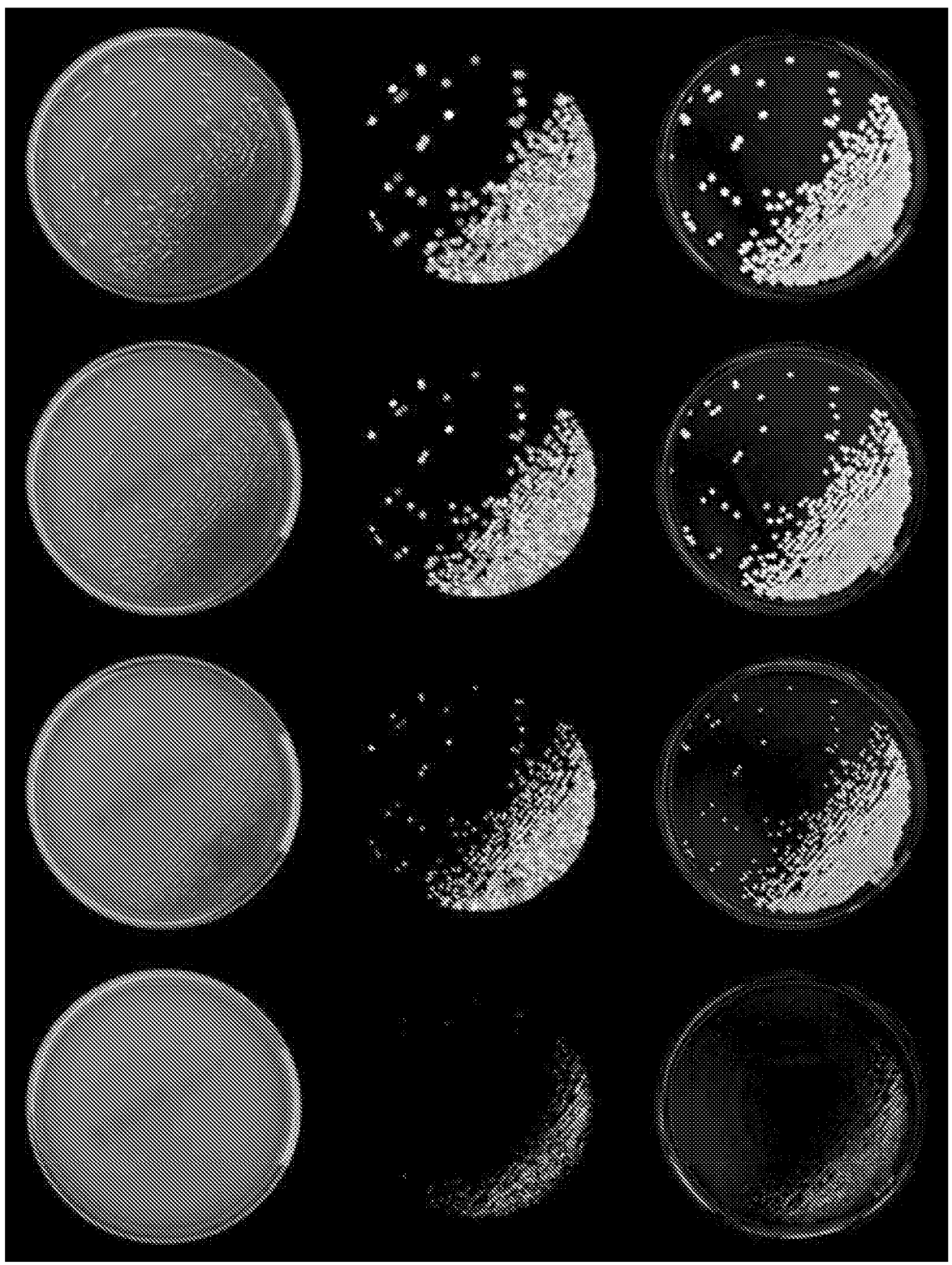
FIG. 13 is a series of images taken over time according to an aspect of the disclosure.

FIG. 13 illustrates the series of images taken over time. In FIG. 13, each row contains a digital image (left), a segmentation result (middle) and a contrast image (right) at a specified time point during incubation: at 8 hours, at 12 hours, at 16 hours and at 20 hours respectively (from bottom to top). Segmentation and contrast images are described in greater detail in the commonly owned, copending patent application titled "COLONY CONTRAST GATHERING," the disclosure of which is incorporated herein in its entirety.

Those skilled in the art will recognize that the results of the above colony estimation techniques, distribution models, confluence ratios and time-series analysis may be used in combination with one another to provide a more accurate estimates, or confirm the accuracy of prior estimates.

Object Features

As discussed above in connection with FIG. 5, features of an object on an imaged plate may be characterized as part of the image analysis performed on the imaged plate. The characterized features may include both static features (pertaining to a single image) and dynamic image (pertaining to a plurality of images).

Static features aim at reflecting object attributes and/or surrounding background at a given time. Static features include the following:

(i) Center of gravity: this is a static feature that provides a center of gravity of an imaged object in a coordinate space (e.g., x-y, polar). The center of gravity of an object, like the polar coordinates of the object, provides invariance in the feature set under given lighting and background conditions. The center of gravity may be obtained by first determining a weighted center of mass for all colonies in the image (M being the binary mask of all detected colonies). The weighted center of mass may be determined based on an assumption that each pixel of the image is of equal value. The center of gravity for a given colony may then be described in x-y coordinates by the following equation (in which E={p|p∈M} (E is the current colony's binary mask), the range for the x-coordinate is [0, image width], the range for the y-coordinate is [0, image height], and each pixel is one unit):

$$igv_{(x,y)}\left(x = \frac{1}{\sum_{p\in E} 1} \times \sum_{p\in E} p_x, y = \frac{1}{\sum_{p\in E} 1} \times \sum_{p\in E} p_y\right) \quad (11)$$

(ii) Polar coordinates: this is also a static feature, and can be used to further characterize locations on the imaged plate, such as a center of gravity. Generally, polar coordinates are measured along a radial axis (d) and an angular axis (Θ), with the coordinates of the plate center being [0,0]. Coordinates d and Θ of $igv_{(x,y)}$ are given (in millimeters for d, and in degrees for Θ) by for following equations (Where k is a pixel density corresponding pixels to millimeters, and "barcode" is a landmark feature of the imaged plate to ensure alignment of the plate with previous and/or future images):

$$d = k \times \text{dist}(igv_{(x,y)}, 0_{(x,y)}) \quad (12)$$

$$\theta = \text{Angle}(\text{barcode}, O_{(x,y)}, igv_{(x,y)}) \quad (13)$$

(iii) Image vector: The two-dimensional polar coordinates may in turn be transformed into a one-dimensional image vector. The image vector may characterize intensity of the pixels of an image as a function of the radial axis (generally, with the center of the colony having the highest intensity) and/or a function of the angular axis. In many cases, the image vector may be more accurate at classifying similarities/distinctions among imaged objects.

(iv) Morphometric features, which describe the shape and size of a given object.

(a) Area: This is a morphometric feature, and can be determined based on the number of pixels in the imaged object (also referred to as a "blob"), not counting holes in the object. When pixel density is available, area may be measured in physical size (e.g., mm$^2$). Otherwise, when pixel density is not available, the total number of pixels may indicate size, and pixel density (k) is set to equal one. In one embodiment, area is calculated using the following equation:

$$A = k^2 \times \Sigma_{p \in E} 1 \quad (14)$$

(b) Perimeter: The perimeter of the object is also a morphometric feature, and can be determined by measuring the edges of the objecting and adding together the total length of the edges (e.g., a single pixel having an area of 1 square unit has a perimeter of 4 units). As with area, length may be measured in terms of pixel units (e.g., when k is not available) or physical lengths (e.g., when k is available). In some circumstances, the perimeter may also include the perimeter of any holes in the object. Additionally, the ladder effect (which results when diagonal edges are digitized into ladder-like boxes) may be compensated by counting inside corners as $\sqrt{2}$, rather than 2. In one embodiment, perimeter may be determined using the following equations:

$$P = k \times \sum_{p \in E} q(n_p) \quad (15)$$

$$n_p = \left\{ \begin{array}{c} t \\ l \; p \; r \\ b \end{array} \right\} \quad (16)$$

(17) if:
{Σ(t∈M,l∈M,r∈M,b∈M)=2,(l∈M≠r ∈M), (t∈M≠b∈M)}
(p is interior and p is a corner)
then: $q(n_p) = \sqrt{2}$ else: $q(n_p) = 4 - \Sigma(t \in M, l \in M, r \in M, b \in M)$ (c) Circularity: The circularity of the object is also a morphometric feature, and can be determined based on a combination of the area and perimeter. In one embodiment, circularity is calculated using the following equation:

$$C = \frac{4\pi A}{P^2} \quad (18)$$

(d) Radius Coefficient of Variation (RCV): This is also a morphometric feature, and is used to indicate variance in radius of the object by taking a ratio between the mean radius $\overline{R}$ of the object in all N directions or angles θ extending from the center of gravity and standard deviation of the radii $\sigma_R$. In one embodiment, this value can be calculated using the following equations:

$$\overline{R} = \frac{\sum_{\theta=0}^{2\pi} R_\theta}{N_\theta} \quad (19)$$

$$\sigma_R = \sqrt{\frac{\sum_{\theta=0}^{2\pi} (R_\theta - \overline{R})^2}{N_\theta - 1}} \quad (20)$$

$$RCV = \frac{\sigma_R}{\overline{R}} \quad (21)$$

(v) Contextual features, which describe the neighborhood topographical relationships of the object under scrutiny to the other detected objects and plate walls edges. For example, in the case of an imaged colony, one contextual feature of the colony may be whether the colony is free, has limited free space, or is competing for access to resources with other surrounding colonies. Such features tend to help classify colonies growing in the same perceived environment, and/or discriminating colonies growing in different environments.

Figure 14:
FIG. 14 is a Voronoï diagram according to an aspect of the disclosure.

(a) Region of Influence: this is a contextual feature that considers the space between an object and its neighboring objects and predicts a region that the object under analysis may expend to occupy (without other, different objects expending to occupy that same region first). The region of influence can be expressed in the form of a Voronoï diagram, such as the diagram shown in FIG. 14, which shows a region of influence (shaded) based on the distance d between a colony 1401 and its neighboring colonies, e.g., 1405. In one embodiment, the distance from the edge of the object to the edge of the region of influence ($D_{NC}$) may be characterized using the following equation:

$$D_{NC} = k \times \text{Min}[\text{dist}(p \in E, \acute{p} \in ME)] \quad (22)$$

(b) Distance to Plate Wall: this is a contextual feature that calculates the distance of the edge of the object from the nearest plate wall ($D_{PW}$). In one embodiment, this distance may be characterized using the following equation:

$$D_{PW} = k \times \text{Min}[\text{dist}(p \in E, \acute{p} \text{ Plate})] \quad (23)$$

(c) Isolation Factor: this is a contextual feature characterizing the relative isolation of a given object based on the object's size and distance to the nearest edge (e.g., of another object, a plate wall). FIGS. 15A-C illustrate aspects of isolation factor. FIG. 15A illustrates an instance in which the nearest edge is distance d from the colony to a plate wall. FIGS. 15B and 15C illustrate an instance in which the nearest edge belongs to another colony. In such a case, a circle is drawn centered around the colony under analysis and then expanded (first small, as in FIG. 15B, then larger as in FIG. 15C) until the circle touches a neighboring colony. In the embodiments of FIGS. 15A-C, the isolation factor (IF) may be characterized using the following equation:

$$IF = \frac{\text{Min}(D_{NC}, D_{PW})}{\overline{R}} \quad (24)$$

(d) Neighboring Occupancy Ratio: this is a contextual feature characterizing the area fraction of a plate's bounded Voronoï region of influence (V) within a given distance d for a given object. In one embodiment, the neighboring occupancy ratio (OR) may be characterized using the following equation (in which for this equation, $E=\{p|p \in V, dist(p, igv_{(x,y)}) < d\}$):

$$OR(d) = \frac{k^2 \times \sum_{p \in E^1}}{\pi(d/2)^2} \quad (25)$$

(e) Relative Neighboring Occupancy Ratio: in some instances, the given distance d may be derived using the mean radius of the object multiplied by a predetermined factor ($d = x \times \overline{R}$). The result is a relative neighboring occupancy ratio (RNOR), and may be derived for a given factor x using the following equations:

$$RNOR(x) = NOR(d) \quad (26)$$

(vi) Spectral features, which describe the light properties of a given object. Color (red, green, and blue light channels; hue, luminance and chrominance, or any other color space transformation), texture and contrast (over time and/or across space) are examples of such features. Spectral features can be derived from images captured at various time points and/or under various illumination conditions during incubation using colony masks, and can further be associated with a Voronoï region of influence for a given colony.
  (a) Channel Image: this is a spectral feature in which a specific color channel (e.g., red (R), green (G), blue (B)) is used to spectrally resolve the image.
  (b) Luma: this is also a spectral feature used to characterize brightness of an image using RGB channels as an input.
  (c) Hue: this is a spectral feature in which an area of the image is characterized as appearing to be similar to a perceived color (e.g., red, yellow, green, blue) or a combination thereof. Hue ($H_2$) is generally characterized using the following equations:

$$H_2 = atan2(\beta, \alpha) \quad (27)$$

$$\alpha = R - \frac{1}{2}(G+B) \quad (28)$$

$$\beta = \frac{\sqrt{3}}{2}(G-B) \quad (29)$$

(d) Chroma: this is a spectral feature for characterizing the colorfulness of an area of an image relative to its brightness if that area were similarly illuminated white. Chroma ($C_2$) is generally characterized using the following equation:

$$C_2 = \sqrt{\alpha^2 + \beta^2} \quad (30)$$

Maximum Contrast:
  [reserved for max contrast] (31)

(vii) Background features, which describe alterations in the media in the neighborhood of the analyzed object. For instance, in the case of an imaged colony, the changes could be caused by microbial growth around the colony (e.g., signs of hemolysis, changes in PH, or specific enzymatic reactions).

Dynamic features aim at reflecting a change of object attributes and/or surrounding background over time. Time series processing allows static features to be related over time. Discrete first and second derivatives of these features provide instantaneous "speed" and "acceleration" (or plateauing or deceleration) of the change in such features to be characterized over time. Examples of dynamic features include the following:

(i) Time series processing for tracking the above static features over time. Each feature measured at a given incubation time may be referenced according to its relative incubation time to allows for the features to be related ones measured at later incubation times. A time series of images can be used to detect objects such as CFUs appearing and growing over time, as described above. Time points for imaging may be preset or defined by an automated process based upon ongoing analysis of previously captured images of the objects. At each time point the image can be a given acquisition configuration, either for the entire series of a single acquisition configuration, or as a whole series of images captured from multiple acquisition configurations.

(ii) Discrete first and second derivatives of the above features for providing instant speed and acceleration (or plateauing or deceleration) of the changes to such features over time (e.g., tracking growth rate, as discussed above):
  (a) Velocity: a first derivative of a feature over time. Velocity (V) of a feature x may be characterized in terms of (x units)/hour, with $\Delta t$ being a span of time expressed in hours, based on the following equations:

$$V = \lim_{\Delta t \to 0} \left(\frac{dx}{dt}\right)^n \quad (32)$$

$$V_{1,0} = \frac{x_1 - x_0}{t_1 - t_0} \quad (33)$$

$$V_{2,1} = \frac{x_2 - x_1}{t_2 - t_1} \quad (34)$$

(b) Acceleration: a second derivative of the feature over time, also the first derivative of Velocity. Acceleration (A) may be characterized based on the following equation:

$$A = \lim_{\Delta t \to 0} \frac{dV}{dt} \quad (35)$$

Dynamic features may include a change in color acquisition signature of an object over the course of incubation. The dynamic change in color allows for further differentiation of objects that may express the same color at a given time point, but different colors at a different time point. Thus, different temporal signatures of color acquisition for two objects would help to conclude that those two objects are different (e.g., different organisms). Conversely, if changes in the color of two objects over time are the same (e.g., follows the same path in a color space), these two objects may be considered to be the same (e.g., the same type or species of organism).

The above image features are measured from the objects or the objects' context and aim at capturing specificities of organisms growing on various media and incubation conditions. The listed features are not meant to be exhaustive and any knowledgeable person in the field could modify, enlarge or restrict this feature set according to the variety of known image processing based features known in the field.

Image features may be collected for each pixel, group of pixels, object, or group of objects, in the image. A distribution of the collected features can be constructed in a histogram in order to more generally characterize regions of the image, or even the entire image. The histogram can itself rely on several statistical features in order to analyze or otherwise process the incoming image feature data, such as those features described in the commonly owned, copending application titled "COLONY CONTRAST GATHERING."

Image Alignment

When multiple images are taken over time, very precise alignment of images is needed in order to obtain valid temporal estimations from them. Such alignment can be achieved by way of a mechanical alignment device and/or algorithms (e.g., image tracking, image matching). Those knowledgeable in the field are cognizant of these solutions and techniques to achieve this goal.

For instance, in cases where multiple images of an object on the plate are collected, the coordinates of an object's location may be determined. Image data of the object collected at a subsequent time may then be associated with the previous image data based on the coordinates, and then used to determine the change in the object over time.

Figure 16A:
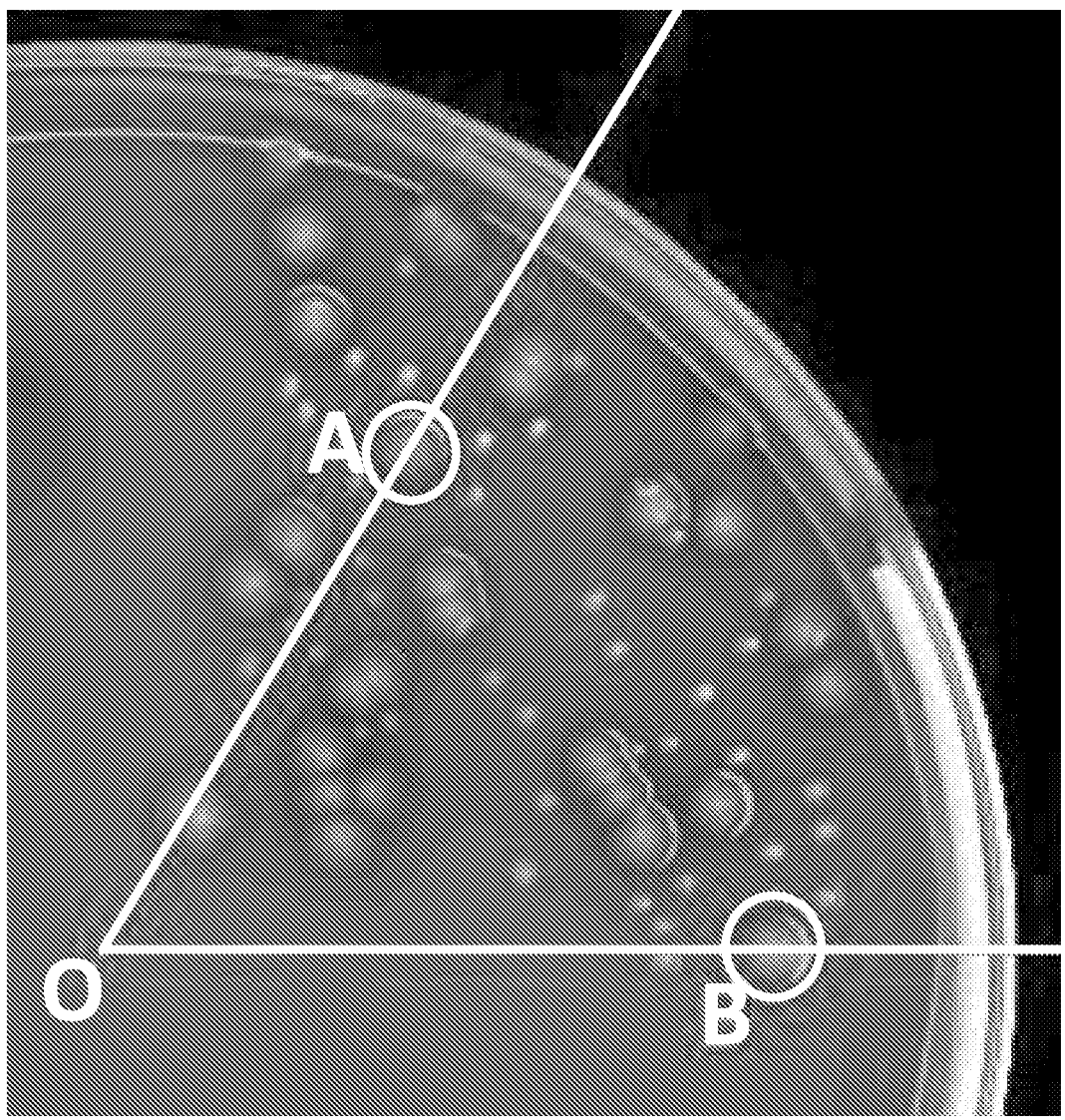
FIGS. 16A and 16B show a section of an imaged plate, with zoomed and reoriented images of sample colonies of the image FIG. 16C are polar transformed images of the zoomed in sections of FIG. 16B, respectively, according to an aspect of the disclosure.
Figure 16B:
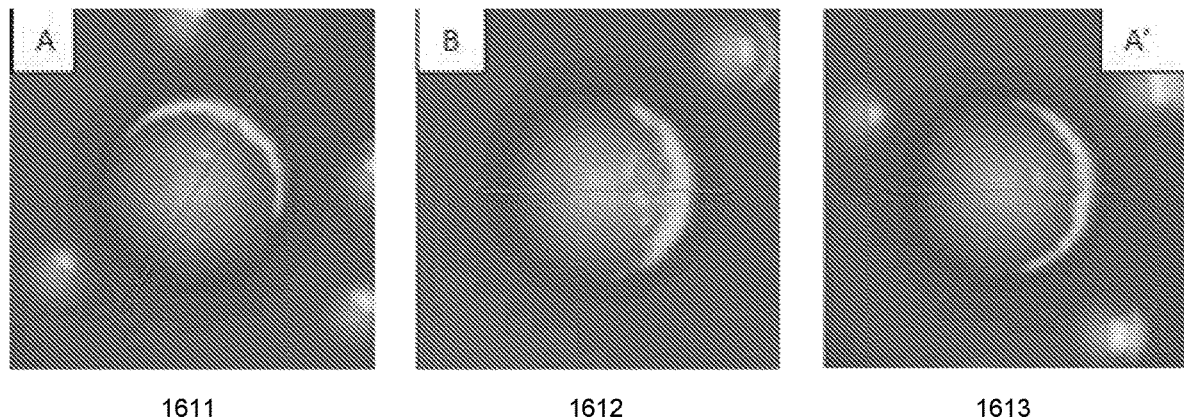

For rapid and valuable usage of images (e.g., when used as input to classifiers), it is important to store the images in a spatial reference to maximize their invariance. As the basic shape descriptor for a colony is generally circular, a polar coordinate system can be used to store colony images. The colony center of mass may be identified as the center of the location of the colony when the colony is first detected. That center point may later serve as origin center for a polar transform of each subsequent image of the colony. FIG. 16A shows a zoomed portion of an imaged plate having a center point "O." Two rays "A" and "B" extending from point "O" are shown (for purposes of clarity) overlaid on the image. Each ray intersects with a respective colony (circled). The circled colonies of FIG. 16A shown in even greater detail in the images 1611 and 1612 FIG. 16B. In FIG. 16B, image 1611 (the colony intersecting ray "A") is reoriented into image 1613 ("A'") such that the radial axis of image 1613 is aligned with that of image 1612, such that the leftmost part of the reoriented image is closest to point "O" of FIG. 16A, and the rightmost part of the reoriented image is farthest from point "O." This polar reorientation allows for easier analysis of the differently oriented (with respect to such factors as illumination) colonies of an imaged plate.

Figure 16C:
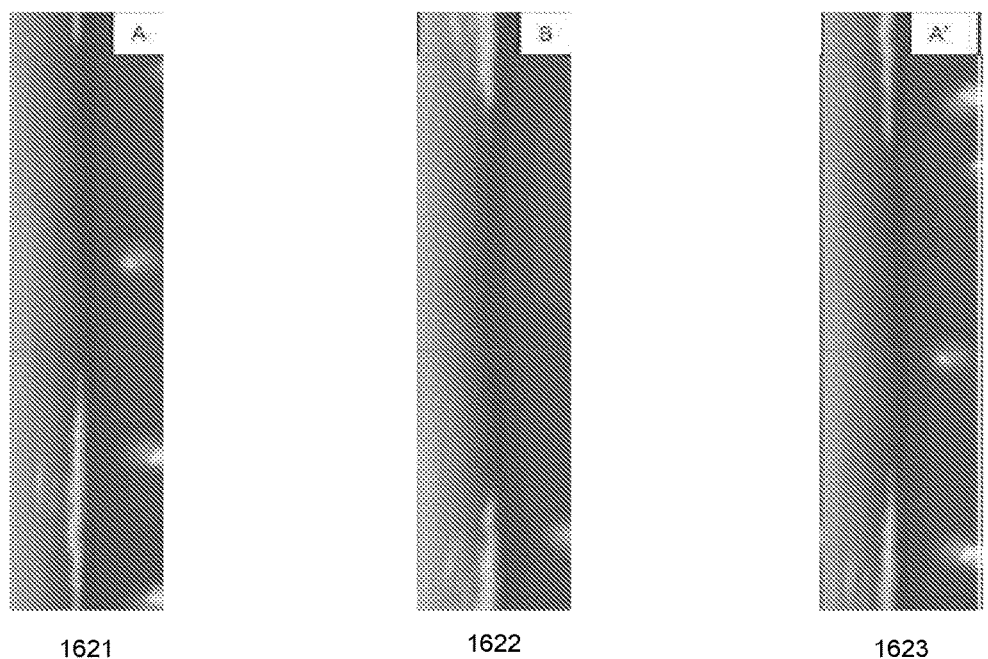

In FIG. 16C, a polar transform is completed for each of the images 1611, 1612 and 1613 of FIG. 16B. In the polar transform images 1621, 1622 and 1623, the radial axis of the respective reoriented images 1611, 1612 and 1613 (extending from the center of each respective imaged colony) are plotted from left to right in the images of FIG. 16C, and the angular axis (of the respective colonies) is plotted from top to bottom For each polar image, summary one-dimensional vector sets can be generated using, for example, shape features and/or histogram features (e.g., average and/or standard deviation of color or intensity of an object) along the radial and/or angular axis. Even if shape and histogram features are mostly invariant when considering rotation, it is possible that some texture features will show significant variations when rotated; thus, invariance is not guaranteed. Therefore, there is a significant benefit to presenting each of the colony images from the same viewpoint or angle illumination-wise, as the objects' texture differences can then be used to discriminate among each other. As illumination conditions mostly show variations linked to angular position around a plate imaging center, the ray going through the colony and plate center (shown as a line in each of images 1611, 1612 and 1613 of FIG. 16) may serve as origin (θ) for each image polar transform.

Improvement of SNR

Under typical illumination conditions, the photon shot noise (statistical variation in the arrival rate of incident photons on the sensor) limits the SNR of the detection system. Modern sensors have a full well capacity that is about 1,700 to about 1,900 electrons per active square micron. Thus, when imaging an object on a plate, the primary concern is not the number of pixels used to image the object but rather the area covered by the object in the sensor space. Increasing the area of the sensor improves the SNR for the imaged object.

Image quality may be improved by capturing the image with illumination conditions under which photon noise governs the SNR (photon noise=$\sqrt{signal}$) without saturating the sensor (maximum number of photons that can be recorded per pixel per frame). In order to maximize the SNR, image averaging techniques are commonly used. These techniques are used to address images with significant brightness (or color) differences since the SNR of dark regions is much lower than the SNR of bright regions, as shown by the following formula:

$$\left( SNR_{dark} = \frac{SNR_{bright}}{\sqrt{\frac{I_{bright}}{I_{dark}}}} \right). \tag{36}$$

in which I is the average current created by the electron stream at the sensor. As colors are perceived due to a difference in absorption/reflection of matter and light across the electromagnetic spectrum, confidence on captured colors will depend upon the system's ability to record intensity with a high SNR. Image sensors (e.g. CCD sensors, CMOS sensors, etc.) are well known to one skilled in the art and are not described in detail herein.

To overcome classical SNR imaging limitations, the imaging system may conduct analysis of an imaged plate during the image acquisition and adjust the illumination conditions and exposure times in real time based on the analysis. This process is described in PCT Publication No. WO2015/114121, incorporated by reference, and generally referred to as Supervised High Quality Imaging (SHQI). The system can also customize the imaging conditions for the various brightness regions of the plate within the different color channels.

For a given pixel x,y of an image, SNR information of the pixel acquired during a current frame N may be combined with SNR information of the same pixel acquired during previous or subsequent acquired frames (e.g., N−1, N+1). By example, the combined SNR is dictated by the following formula:

$$SNR_{x,y,N+1}' = \sqrt{SNR_{x,y,N}'^2 + SNR_{x,y,N+1}^2} \tag{37}$$

After updating the image data with a new acquisition, the acquisition system is able to predict the best next acquisition time that would maximize SNR according to environmental constraints (e.g. minimum required SNR per pixel within a region of interest). For example, averaging 5 images captured in non-saturating conditions will boost the SNR of a dark region (10% of max intensity) by √5, when merging the information of two images captured in bright and dark conditions optimum illumination will boost the dark regions SNR by √11 in only two acquisitions.

Applications

The present disclosure is based largely on testing performed in saline at various dilutions to simulate typical urine reporting amounts (CFU/ml Bucket groups). A suspension for each isolate was adjusted to a 0.5 McFarland Standard and used to prepare dilutions at estimated $1\times10^6$, $1\times10^5$, $5\times10^4$, $1\times10^4$, $1\times10^3$, and $1\times10^2$ CFU/ml suspension in BD Urine Vacutainer tubes (Cat. No. 364951). Specimen tubes were processed using Kiestra InoqulA (WCA1) with the standard urine streak pattern—#4 Zigzag (0.01 ml dispense per plate).

All acquired images were corrected for lens geometrical and chromatic aberrations, spectrally balanced, with known object pixel size, normalized illumination conditions and high signal to noise ratio per band per pixel. Suitable cameras for use in the methods and systems described herein are well known to one skilled in the art and not described in detail herein. As an example, using a 4-megapixel camera to capture a 90 mm plate image should allow enumeration up to 30 colonies/mm² local densities ($>10^5$ CFU/plate) when colonies are in the range of 100 μm in diameter with adequate contrast.

The magnetic rolling bead used for streaking the sample plates was 5 mm in diameter, 15.7 mm in circumference and 78 mm² in surface area. The average surface of contact with the media is about 4 mm² which represents a contact disk of roughly 2.2 mm in diameter.

The following media were used evaluate the contrast of colonies grown thereon:

TSAII 5% Sheep blood (BAP): a non selection media with worldwide usage for urine culture.

BAV: used for colony enumeration and presumptive ID based on colony morphology and hemolysis.

MacConkey II Agar (MAC): a selective media for most common Gram negative UTI pathogens. MAC is used for differentiation of lactose producing colonies. MAC also inhibits Proteus swarming. BAP and MAC are commonly used worldwide for urine culture. Some media are not recommended for use for colony counting due to partial inhibition of some gram negatives.

Colistin Nalidixic Acid agar (CNA): a selective media for most common Gram positive UTI pathogens. CNA is not as commonly used as MAC for urine culture but helps to identify colonies if over-growth of Gram negative colonies occurs.

CHROMAgar Orientation (CHROMA): a non-selection media used worldwide for urine culture. CHROMA is used for colony enumeration and ID based on colony color and morphology. *E. coli* and *Enterococcus* are identified by the media and do not require confirmatory testing. CHROMA is used less than BAP due to cost. For mixed samples, CLED media was also used.

Cystine Lactose Electrolyte-Deficient (CLED) Agar: used for colony enumeration and presumptive ID of urinary pathogens based on lactose fermentation.

The Specimen Processing BD Kiestra™ InoqulA™ was used to automate the processing of bacteriology specimens to enable standardization and ensure consistent and high quality streaking. The BD Kiestra™ InoqulA™ specimen processor uses a magnetic rolling bead technology to streak media plates using customizable patterns.

Figure 17:
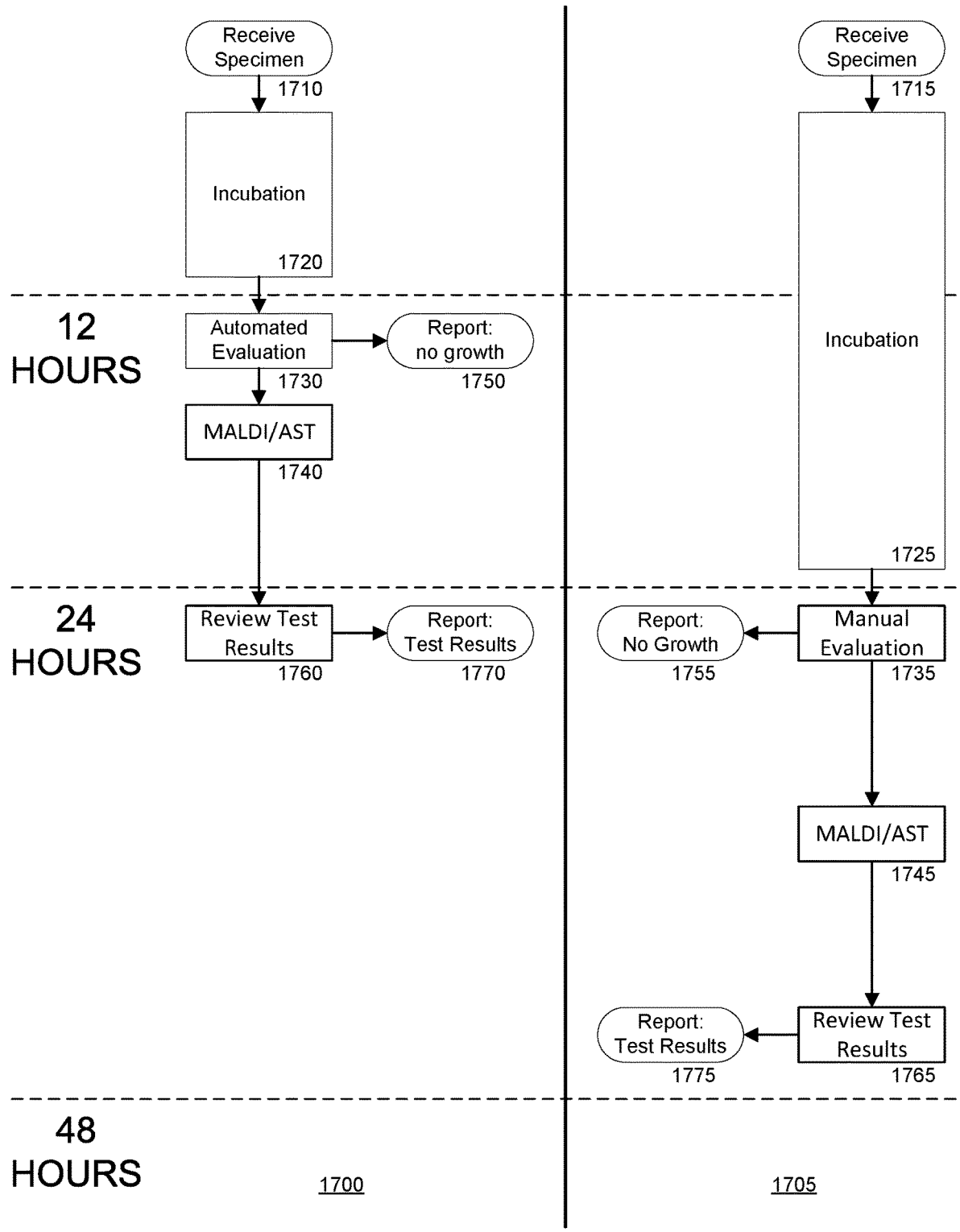
FIG. 17 is a flow chart comparing the timeline of the routine of FIG. 2 to the timeline of a comparable manually-performed process.

FIG. 17 shows a pair of flow charts comparing a timeline of an automated test process 1700 (e.g., the routine 200 of FIG. 2) to a timeline of a comparable manually-performed test process 1705. Each process begins with the specimen for testing being received at a laboratory 1710, 1715. Each process then proceeds with incubation 1720, 1725, during which the specimen may be imaged several time. In the automated process, an automated evaluation 1730 is made after approximately 12 hours of incubation, after which time it can be definitively determined whether there is significant growth or no growth (or normal growth) in the specimen 1740. As shown from the above disclosure, the use of statistical methods to classify and count colonies in the automated process greatly improves the ability to determine whether there has been significant growth, even after only 12 hours. By contrast, in the manual process, a manual evaluation 1735 cannot be made until nearly 24 hours into the incubation process. Only after 24 hours can it be definitively determined whether there is significant growth or no growth (or normal growth) in the specimen 1745.

The use of an automated process also allows for faster AST and MALDI testing. Such testing 1750 in an automated process can begin soon after the initial evaluation 1730, and the results can be obtained 1760 and reported 1775 by the 24 hour mark. By contrast, such testing 1755 in a manual process often does not begin until close to the 36 hour mark, and takes an additional 8 to 12 hours to complete before the data can be reviewed 1765 and reported 1775.

Altogether, the manual test process 1705 is shown to take up to 48 hours, requires a 18-24 hour incubation period, only after which is the plate evaluated for growth, and further has no way to keep track of how long a sample has been in incubation. By contrast, because the automated test process 1700 can detect even relatively poor contrast between colonies (compared to background and each other), and can conduct imaging and incubation without a microbiologist having to keep track of timing, only 12-18 hours of incubation is necessary before the specimen can be identified and prepared for further testing (e.g., AST, MALDI), and the entire process can be completed within about 24 hours. Thus, the automated process of the present disclosure, aided with the contrast processing described herein, provides faster testing of samples without adversely affecting the quality or accuracy of the test results.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An automated method for evaluating microbial growth on plated media, the method comprising:
    providing a culture media inoculated with a biological sample;
    incubating the inoculated culture media;
    following incubation, obtaining a first image of the inoculated culture media at a first time (t1);
    after further incubation, obtaining a second image of the inoculated culture media at a second time (t2);
    aligning the first image with the second image, such that coordinates of a pixel in the second image are about the same as the coordinates of a corresponding pixel in the first image;
    determining contrast information of the second image, the contrast information including:

spatial contrast information indicating differences between pixels of the second image; and temporal contrast information indicating differences between pixels of the second image and corresponding pixels of a previous image;

comparing image features of the second image with image features of the first image based on the contrast information;

classifying image features of the second image as colony candidates based on image feature changes from time t1 to time t2;

for colony candidates determined to be from a common microorganism in the biological sample inoculated on the culture media, counting said colony candidates; and determining whether a number of counted colonies meets or exceeds a threshold count value stored in memory and indicative of significant growth.

2. The method of claim 1 wherein if the number of counted colonies meets or exceeds the threshold count value further comprising:

identifying at least one colony using matrix-assisted laser desorption ionization (MALDI); and testing said at least one colony for antibacterial susceptibility; and outputting a report containing the MALDI and antibacterial susceptibility test results.

3. The method of claim 2 wherein a plurality of threshold count values are stored in memory, each threshold count value associated with a different microorganism.

4. The method of claim 3 wherein classifying image features of the second image as colony candidates comprises:

identifying an object in the second image based on the contrast information; and obtaining one or more object features of the identified object from pixel information associated in the first and second images, wherein the object is classified as a colony candidate based on the one or more object features.

5. The method of claim 4 further comprising, for each colony candidate, determining whether the colony candidate is a colony or an artifact based on pixel information associated with the colony candidate, wherein colony candidates that are determined to be artifacts are not counted.

6. The method of claim 5 wherein determining whether a colony candidate is a colony or an artifact further comprises determining whether the colony candidate is present in each of the first and second images and larger in the second image than the first image by a threshold growth factor, wherein a colony candidate that is present in both images and is larger in the second image by at least the threshold growth factor is classified as a colony.

7. The method of claim 6 wherein determining whether a colony candidate is a colony or an artifact further comprises, for a colony candidate that is present in the second image and not the first image:

obtaining one or more object features of the identified object from the pixel information associated with the object in the second image;

determining a probability that the colony candidate is a colony based on the one or more object features; and comparing the determined probability to a predefined threshold probability value, wherein, if the determined probability is greater than the predefined threshold probability value, then the colony candidate is classified as a colony.

8. The method of claim 7 further comprising:

classifying (i) colony candidates that are present in both images and not larger in the second image, and (ii) colony candidates that are present in first image and not in the second image, as definite artifacts;

classifying colony candidates that are present in each of the first and second images and larger in the second image by the threshold growth factor as definite colonies; and calculating an artifact probability value based on a combination of the definite artifacts and the definite colonies, wherein the determined probability that a colony candidate is a colony is further based on artifact probability.

9. The method of claim 8 wherein the one or more object features comprise at least one of object shape, object size, object edge and object color.

10. The method of claim 9 wherein the one or more object features comprise at least one of color, hue, luminance and chrominance of the pixels of the object.

11. The method of claim 10 further comprising obtaining background feature information, wherein background feature information comprises media type and media color, and wherein the object is classified as a colony candidate based further on the background feature information.

12. The method of claim 11 wherein aligning the first image with the second image involves assigning polar coordinates to pixels of each of the first and second images such that the polar coordinates of a pixel in the second image are the same as the polar coordinates of a corresponding pixel in the first image.

13. A computer-readable memory storage medium having program instructions encoded thereon configured to cause a processor to perform a method of evaluating microbial growth on plated media, the method comprising:

following incubation of a culture media inoculated with a biological sample for first predetermined time, instructing an image acquisition device to obtain a first image of the inoculated media at a first time (t1);

after further incubation a culture media inoculated with a biological sample for a second predetermined time, obtaining a second image of the inoculated media at a second time (t2);

aligning the first image with the second image, such that the coordinates of a pixel in the second image are about the same as the coordinates of a corresponding pixel in the first image;

comparing image features of the second image with image features of the first image;

classifying image features of the second image as colony candidates based on image feature changes from time t1 to time t2 wherein classifying image features of the second image as colony candidates comprises:

i) determining contrast information of the second image, the contrast information including at least one of:
   a) spatial contrast information indicating differences between pixels of the second image; and
   b) temporal contrast information indicating differences between pixels of the second image and corresponding pixels of a previous image;

ii) identifying an object in the second image based on the contrast information; and iii) obtaining one or more object features of the identified object from pixel information associated in the first and second images, wherein the object is classified as a colony candidate based on the object features;

for colony candidates determined to be from a common microorganism in the biological sample inoculated on the culture media, counting said colony candidates; and determining whether the number of counted colonies meets or exceeds a threshold count value stored in memory and indicative of significant growth.

14. A system for evaluating growth in a culture media inoculated with a biological sample, the system comprising:

an image acquisition device for capturing digital images of the culture media;

memory storing information regarding predicted amounts of microbial growth for one or more different organisms in one or more different culture media; and one or more processors operable to execute instructions to perform a method comprising:

following incubation of a culture media inoculated with a biological sample for first predetermined time, instructing an image acquisition device to obtain a first image of the inoculated media at a first time (t1);

after further incubation a culture media inoculated with a biological sample for a second predetermined time, obtaining a second image of the inoculated media at a second time (t2);

aligning the first image with the second image, such that the coordinates of a pixel in the second image are about the same as the coordinates of a corresponding pixel in the first image;

comparing image features of the second image with image features of the first image;

classifying image features of the second image as colony candidates based on image feature changes from time t1 to time t2;

wherein classifying image features of the second image as colony candidates comprises:

i) determining contrast information of the second image, the contrast information including at least one of:
  a) spatial contrast information indicating differences between pixels of the second image; and
  b) temporal contrast information indicating differences between pixels of the second image and corresponding pixels of a previous image;

ii) identifying an object in the second image based on the contrast information; and iii) obtaining one or more object features of the identified object from pixel information associated in the first and second images wherein the object is classified as a colony candidate based on the object features;

for colony candidates determined to be from a common microorganism in the biological sample inoculated on the culture media, counting said colony candidates; and determining whether the number of counted colonies meets or exceeds a threshold count value stored in memory and indicative of significant growth.

* * * * *